US011504646B2

(12) United States Patent
Singh et al.

(10) Patent No.: US 11,504,646 B2
(45) Date of Patent: Nov. 22, 2022

(54) DEPTH FILTERS FOR DISPOSABLE BIOTECHNOLOGICAL PROCESSES

(71) Applicant: EMD Millipore Corporation, Burlington, MA (US)

(72) Inventors: Nripen Singh, Acton, MA (US); Kwok-Shun Cheng, Nashua, NH (US)

(73) Assignee: EMD Millipore Corporation, Burlington, MA (US)

( * ) Notice: Subject to any disclaimer, the term of this patent is extended or adjusted under 35 U.S.C. 154(b) by 0 days.

(21) Appl. No.: 17/008,690

(22) Filed: Sep. 1, 2020

(65) Prior Publication Data

US 2020/0398187 A1    Dec. 24, 2020

Related U.S. Application Data

(60) Division of application No. 16/058,258, filed on Aug. 8, 2018, now Pat. No. 10,786,754, which is a
(Continued)

(51) Int. Cl.
*B01D 15/12* (2006.01)
*B01D 15/38* (2006.01)
(Continued)

(52) U.S. Cl.
CPC ....... *B01D 15/125* (2013.01); *B01D 15/3809* (2013.01); *C02F 1/001* (2013.01);
(Continued)

(58) Field of Classification Search
CPC .............. B01D 15/125; B01D 15/3809; B01D 2239/025; B01D 2239/0428;
(Continued)

(56) References Cited

U.S. PATENT DOCUMENTS 4,816,567 A    3/1989 Cabilly et al.
5,091,178 A    2/1992 Hellstrom et al.
(Continued)

FOREIGN PATENT DOCUMENTS

CN    101039734 A    9/2007
EP    0420937 B1    11/1994
(Continued)

OTHER PUBLICATIONS

International Preliminary Report on Patentability received for PCT Patent Application No. PCT/US2012/044806, dated Jan. 23, 2014, 7 pages.
(Continued)

*Primary Examiner* — Liam Royce
(74) *Attorney, Agent, or Firm* — EMD Millipore Corporation

(57) ABSTRACT

A process for the primary clarification of feeds, including chemically treated flocculated feeds, containing the target biomolecules of interest such as mAbs, mammalian cell cultures, or bacterial cell cultures, using a primary clarification depth filtration device without the use of a primary clarification centrifugation step or a primary clarification tangential flow microfiltration step. The primary clarification depth filtration device contains a porous depth filter having graded porous layers of varying pore ratings. The primary clarification depth filtration device filters fluid feeds, including chemically treated flocculated feeds containing flocculated cellular debris and colloidal particulates having a particle size distribution of approximately about 0.5 μm to 200 μm, at a flow rate of about 10 litres/m²/hr to about 100 litres/m²/hr. Kits and methods of using and making the same are also provided.

10 Claims, 5 Drawing Sheets

Related U.S. Application Data continuation of application No. 13/538,649, filed on Jun. 29, 2012, now abandoned.

(60) Provisional application No. 61/571,994, filed on Jul. 8, 2011.

(51) Int. Cl.
| | | |
|---|---|---|
| *C02F 1/00* | (2006.01) | |
| *C02F 1/52* | (2006.01) | |
| *C07K 1/34* | (2006.01) | |
| *C02F 1/56* | (2006.01) | |
| *C02F 103/34* | (2006.01) | |

(52) U.S. Cl.
CPC ............... *C02F 1/52* (2013.01); *C07K 1/34* (2013.01); *B01D 2239/025* (2013.01); *B01D 2239/0428* (2013.01); *B01D 2239/065* (2013.01); *C02F 1/56* (2013.01); *C02F 2103/343* (2013.01)

(58) Field of Classification Search
CPC .. B01D 2239/065; B01D 29/01; B01D 39/08; B01D 61/00; C07K 1/34; C07K 361/14; C07K 361/18; C02F 1/001; C02F 1/52; C02F 1/56; C02F 2103/343; C12M 1/123; C12M 1/10; C12M 1/12

See application file for complete search history.

(56) References Cited

U.S. PATENT DOCUMENTS

| | | | |
|---|---|---|---|
| 5,091,313 | A | 2/1992 | Chang |
| 5,190,657 | A | 3/1993 | Heagle et al. |
| 5,298,165 | A | 3/1994 | Oka et al. |
| 5,622,700 | A | 4/1997 | Jardieu et al. |
| 5,672,347 | A | 9/1997 | Aggarwal et al. |
| 5,714,338 | A | 2/1998 | Wai Fei et al. |
| 5,736,137 | A | 4/1998 | Anderson et al. |
| 6,307,013 | B1 | 10/2001 | Chivers |
| 7,531,632 | B2 | 5/2009 | Perreault |
| 2002/0132985 | A1 | 9/2002 | Mamidi et al. |
| 2003/0201229 | A1 | 10/2003 | Siwak et al. |
| 2004/0118765 | A1 | 6/2004 | Yavorsky et al. |
| 2004/0118766 | A1 | 6/2004 | Pulek et al. |
| 2004/0124146 | A1 | 7/2004 | Dao et al. |
| 2005/0205489 | A1 | 9/2005 | Siwak |
| 2006/0107639 | A1 | 5/2006 | Hamlin et al. |
| 2006/0261000 | A1* | 11/2006 | Bassett .............. B01D 39/1661 210/435 |
| 2007/0193938 | A1* | 8/2007 | Yavorsky ............... B01J 20/20 502/416 |
| 2009/0232737 | A1 | 9/2009 | Moya et al. |
| 2010/0264087 | A1 | 10/2010 | Dholakia |
| 2011/0163043 | A1 | 7/2011 | Kayamori et al. |
| 2013/0012689 | A1 | 1/2013 | Singh et al. |

FOREIGN PATENT DOCUMENTS

| | | |
|---|---|---|
| JP | 2005-263803 A | 9/2005 |
| JP | 2009-508486 A | 3/2009 |
| JP | 2009534030 A | 9/2009 |
| WO | 1993/004173 A1 | 3/1993 |
| WO | 1995/019181 A1 | 7/1995 |
| WO | 1997/026912 A2 | 7/1997 |
| WO | 1998/051793 A1 | 11/1998 |
| WO | 2007/035283 A1 | 3/2007 |
| WO | 2007/106078 A2 | 9/2007 |
| WO | 2007/123961 A2 | 11/2007 |
| WO | 2010/048192 A2 | 4/2010 |
| WO | 2010/074702 A1 | 7/2010 |
| WO | 2010/074773 A1 | 7/2010 |
| WO | 2010/074953 A1 | 7/2010 |
| WO | 2010/151447 A1 | 12/2010 |
| WO | 2012/054679 A1 | 4/2012 |
| WO | 2013/009491 A2 | 1/2013 |
| WO | 2013/184937 A1 | 12/2013 |

OTHER PUBLICATIONS

International Search Report and Written Opinion received for PCT Patent Application No. PCT/US2012/044806, dated Feb. 26, 2013, 11 pages.

Supplemental European Search Report received for European Patent Application No. 12811005.3, dated Jan. 28, 2015, 3 pages.

Aldington et al., "Scale-Up of Monoclonal Antibody Purification Processes", Journal of Chromatography B, vol. 848, 2007, pp. 64-78.

Butler, M. "A Comparative Review of Microcarriers Available For The Growth of Anchorage-Dependent Animal Cells", Animal Cell Biotechnology, vol. 3 (eds Griffiths, B. and Spier, R.E.), 1988, pp. 283-303.

Carter et al., "Humanization of an Anti-p185HER2 Antibody For Human Cancer Therapy", Proc. Natl. Acad. Sci. USA, vol. 89, 1992, pp. 4285-4289.

Chartain et al., "Development and Production of Commercial Therapeutic Monoclonal Antibodies in Mammalian Cell Expression Systems: An Overview of the Current Upslieam Technologies", Current Pharmaceutical Biotechnology, vol. 9, 2008, pp. 447-467.

Choy et al., "Percentage of Anti-CD4 Monoclonal Antibody-Coated lymphocytes in the Rheumatoid Joint is Associated with Clinical Improvement. Implications for the Development of Immunotherapeutic Dosing Regimens", Arthritis & Rheumatism, vol. 39, No. 1, 1996, pp. 52-56.

Clackson et al., "Making Antibody Fragments Using Phage Display Libraries", Nature, vol. 352, Aug. 15, 1991, pp. 624-628.

Dhainaut et al., "CDP571, A Humanized Antibody to Human Tumor Necrosis Factor-Alpha: Safety, Pharmacokinetics, Immune Response, and Influence of the Antibody on Cytokine Concenlialions in Patients with Septic Shock", Critical Care Medicine, vol. 23, No. 9, 1995, pp. 1461-1469.

Graziano et al., "Construction and Characterization of a Humanized anti-γ-lg receptor type I (Fc gamma RI) monoclonal antibody", The Journal of Immunology, vol. 155, No. 10, 1995, pp. 4996-5002.

Hoffman, Allan S., ""Intelligent" Polymers in Medicine and Biotechnology", Artificial Organs, vol. 19, No. 5, 1995, pp. 458-467.

Hoffman, Allan S., "Applications of Thermally Reversible Polymers And Hydrogels in Therapeutics and Diagnostics", Journal of Controlled Release, vol. 6, 1997, pp. 297-305.

Hoffman, Allan S., "Bioconjugates of Intelligent Polymers and Recognition Proteins for Use in Diagnostics and Affinity Separations", Clinical Chemistry, vol. 46, No. 9, 2000, pp. 1478-1486.

Hoffman, Allan S., "Intelligent Polymers. In: Park K, Ed. Controlled Drug Delivery", Washington: ACS Publications, 1997, pp. 485-498.

Jones et al., "Replacing The Complementarity-Determining Regions in a Human Antibody With Those From a Mouse", Nature, vol. 321, May 29, 1986, pp. 522-525.

Kohler et al., "Continuous Cultures of Fused Cells Secreting Antibody of Predefined Specificity", Nature, vol. 256 (Attached version of document is reprinted with permission in The Journal of Immunology, 2005, vol. 174, pp. 2453-2455), Aug. 7, 1975, pp. 495-497.

Lorenz et al., "In Vivo Blockade of TNF-alpha by Intravenous Infusion of a Chimeric Monoclonal TNF-α Antibody in Patients with Rheumatoid Arthritis. Short Term Cellular and Molecular Effects", The Journal of Immunology, vol. 156, No. 4, 1996, pp. 1646-1653.

Marks et al., "By-Passing Immunization : Human Antibodies From V-Gene Libraries Displayed on Phage", Journal of Molecular Biology, vol. 222, No. 3, Dec. 5, 1991, pp. 581-597.

Mohamed et al., "Efficient Use of Fibrous Structures in Filtration", Environmental protection technology Series, EPA-600/2-76-204, 1976.

Morrison et al., "Chimeric Human Antibody Molecules: Mouse Antigen-Binding Domains With Human Constant Region Domains", Proc. Nati. Acad. Sci. USA, vol. 81, 1984, pp. 6851-6855.

(56) References Cited

OTHER PUBLICATIONS

Chandler et al., "Clarification of Yeast Cell Suspensions by Depth Filtration", Biotechnology Progress, vol. 21, No. 5, Sep. 5, 2005, pp. 1552-1557.
Presta, Leonard G, "Antibody Engineering", Current Opinion in Structural Biology, vol. 2, No. 4, 1992, pp. 593-596.
Presta et al. "Humanization of an Antibody Directed Against IgE", The Journal of Immunology, vol. 151, No. 5, 1993, pp. 2623-2632.
Riechmann et al., "Reshaping Human Antibodies for Therapy", Nature, vol. 332, Mar. 24, 1988, pp. 323-327.
Riske et al., "The Use of Chitosan as a Flocculant in Mammalian Cell Culture Dramatically Improves Clarification Throughput Without Adversely Impacting Monoclonal Antibody Recovery", Journal of Biotechnology, vol. 128, No. 4, Mar. 10, 2007, pp. 813-823.
Singhvi et al., "Clarification of Animal Cell Culture Process Fluids Using Depth Microfiltration", BioPharm, vol. 9, No. 4, 1996, pp. 35-41.
Trexler-Schmidt et al., "Purification Strategies to Process 5 g/L Titers of Monoclonal Antibodies", Available online at <http://www.modernmedicine.com/modernmedicine/article/articleDetail.jsp?id=585662>, Mar. 2, 2009, 12 pages.
Van Reis et al., "Bioprocess Membrane Technology", Journal of Membrane Science, vol. 297, Jul. 5, 2007, pp. 16-50.
Yigzaw et al., "Exploitation of the Adsorptive Properties of Depth Filters for Host Cell Protein Removal During Monoclonal Antibody Purification", Biotechnology Progress, vol. 22, 2006, pp. 288-296.
Kopecek et al., "Hydrogel Biomaterials: A Smart Future?", Biomaterials, vol. 28, 2007, pp. 5185-5192.
Roy et al., "Smart Polymeric Materials: Emerging Biochemical Applications", Chemistry Department, vol. 10, Indian Institute of Technology, 2003, pp. 1161-1171.

* cited by examiner

DEPTH FILTERS FOR DISPOSABLE BIOTECHNOLOGICAL PROCESSES

CROSS-REFERENCED TO RELATED APPLICATIONS

This application is a Divisional of U.S. application Ser. No. 16/058,258 filed on Aug. 8, 2018, which is a Continuation of U.S. application Ser. No. 13/538,649, filed on Jun. 29, 2012, which claims the benefit of U.S. Provisional Patent Application No. 61/571,994, filed on Jul. 8, 2011, the entire contents of each of which are incorporated by reference herein.

DESCRIPTION OF THE INVENTION

Field of the Invention

In general, the present invention relates to the primary clarification of feeds. In certain specific embodiments, the invention provides a primary clarification depth filtration process of feeds, feedstreams, feedstocks, cell culture broths and the like, which utilizes a primary clarification depth filtration device without the use of a primary clarification centrifugation step or primary clarification tangential flow microfiltration step. In other embodiments, the invention provides primary clarification depth filtration process of chemically treated feeds in which the cell mass has been flocculated into larger aggregates.

BACKGROUND OF THE INVENTION

Manufacturing pharmaceutical-grade biomolecules, including proteins such as monoclonal antibodies (mAbs), is a complex manufacturing process comprised of multiple filtration, centrifugation, and chromatography techniques designed to produce high quality products for patients. The clarification of cell culture harvests and high-solids feedstocks can be a daunting task due to the large volumes of harvest from modern production batch bioreactors (≤25,000 L) and high cell densities that often require primary, as well as secondary clarification prior to the subsequent chromatography operations. And as such, harvest and clarification schemes for the production processes of cell culture harvests and high-solids feedstocks, such as mammalian cells and mAbs, are the product of much evolution and evaluation carried out over the last 20 years or so.

Harvest techniques for mammalian cell culture and mAbs are now routinely expected to operate with high yields (>95%) and minimal cell disruption. As product molecule titers have increased, the higher cell mass and larger amounts of product create challenges for the downstream purification steps. Higher cell densities result in difficulties during clarification and sterile filtration. Higher product concentrations generally result in increased impurity load and the need for larger chromatography installations. As such, improvements in the form of gains in efficiency and throughput are greatly sought after.

Increasing demand and growth therapeutic mAbs have fueled efforts towards increasing product production, quality, process efficiency, and cost-effectiveness for production of industrial therapeutic monoclonal antibodies. The past decade has witnessed considerable growth in production, upstream cell culture product titers and technical advancement in the characterization of impurities and contaminants.

Primary clarification of feeds, feedstreams, feedstocks, cell culture broths and the like, including high solids feeds, such as those containing mAbs and mammalian cell culture feedstocks, remove large amounts of biomass, particularly whole cells and other larger cellular debris, followed by secondary clarification which removes smaller colloidal particulates and other particles that impair the capacity of downstream filters. Centrifugation is typically the primary clarification step in the production processes of mAbs and mammalian cell culture broths and feedstocks.

mAb manufacturers have invested a great deal of time and effort increasing the product titer of a feedstock. However, while higher titers increase cell culture productivity, it also produces feedstocks with larger amounts of biomass and cell debris content. Feeds containing such larger amounts of biomass and cell debris can produce high turbidity centrate after centrifugation. High turbidity centrates often reduce the throughput of the secondary clarification depth filter and the subsequent sterile filter used downstream of the centrifuge. The reduced throughput causes a range of problems from increased process cost to deviations in process procedures due to plugging of filters and long processing delays. Finally, the need for primary clarification using a centrifuge requires extensive, validated cleaning procedures between runs to attempt to reduce the risk of cross contamination between batches and therapeutic molecular species.

This is particularly problematic at pilot or clinical scale biotherapeutic production where it is desirable to process multiple products in a relatively short time. The centrifuge cleaning procedures slow down the pilot plant's ability to change over to the production of a different biomolecule and greatly increase the risk of cross contamination between production runs. In addition, centrifugation cannot efficiently remove all particulates and cellular debris from these feedstocks in the primary clarification step, hence the need for the secondary clarification step utilizing depth filtration after the centrifugation step, but prior to the subsequent chromatographic steps.

Alternatively, successive filtration runs have proven useful in removing different-sized cell and cellular debris from feedstocks, but typically the volumetric throughputs limit the application to smaller volumes (<1000 L) where the filter installation has a reasonable size. The use of filtration greatly reduces the risk of cross contamination and eliminates the need for cleaning and cleaning validation between runs due the disposable nature of filtration devices. Unfortunately, the low throughput requires a large number of filter units which can reduce filtration yields because each successive step results in the loss of a portion of the feed solution through hold-up volumes of the filter device and equipment.

In order to further enhance clarification performance, throughput and downstream filtration operations, the flocculation of a cell culture harvests have been used. Flocculants are a class of materials that can aggregate and agglutinate fine particles from a solution, resulting in their settling from the liquid phase and a reduction in solution turbidity.

Flocculation can be accomplished in a variety of ways including polymer treatment, chemical treatment (changes in pH) or the addition of a surfactant. Precipitation using flocculants can be used to selectively remove impurities while leaving the protein product in the solution. However, flocculants have not been widely used in the clarification of mAbs, mammalian cells, and other bimolecular cellular materials of interest feedstocks.

Flocculation of cell culture harvests by chemicals require the use of either acids, such as acetic acid, or polymers such as chitosan, polysaccharides, polyamines or polyacrylamides. Flocculation has been used as an alternative separation technology to enhance centrifuge clarification throughput and centrate quality, thereby improving the downstream filtration operations. While chemical flocculation is quite effective in agglomerating cellular debris and cellular contaminants (host cell proteins and DNA), the resulting flocculated suspension is generally not easily separable by ordinary filtration methods without the use of a centrifuge prior to filtration.

Flocculants precipitate cells, cell debris and proteins because of the interaction between the charges on the proteins and charges on the polymer (e.g. polyelectrolytes), creating insoluble complexes, and subsequent bridging of insoluble complexes either by residual charge interaction or through hydrophobic patches on the complexes to form larger clusters. In order to remove these large clusters, a centrifuging step or tangential flow microfiltration is the primary mode of clarification followed by the secondary clarification step whereby depth filtration is widely used in the clarification of cell culture broth prior to the capture chromatography step. Since centrifugation cannot deliver a particle-free centrate, depth filter (secondary depth filtration) and sterile filter need to be installed further downstream.

Tangential flow microfiltration (also called cross-flow microfiltration) competes with centrifugation for the harvest and clarification of mAbs and therapeutic products from mammalian cell culture. One advantage this technique offers is the creation of a particle-free harvest stream that requires minimal additional filtration. However, tangential flow microfiltration membranes used for cell culture harvests are often plagued with the problem of membrane fouling (i.e., irrecoverable declines in membrane flux) and typically require strict complex operating condition followed by a thorough cleaning regimen (as is also the case with a centrifuge) for the membranes after each use. The use of optimized membrane chemistry, with more hydrophilic tangential flow microfiltration membranes generally being somewhat less susceptible to significant fouling, to address this issue.

Traditionally, flocculation is generally used to agglomerate non-deformable solid particles. For example, dilute suspensions of submicron sized clay or titanium dioxide particles, which are very difficult to filter because of their small particle size, can be chemically flocculated and easily separated easily by, because the size of these submicron particles size greatly increases by the formation of agglomerated flocs., which settle more quickly, and thereby filter faster because of large flow channels inside the cake.

However, when chemical flocculation is applied to mAb feedstocks or other biomolecule/cellular feedstocks, the resulting agglomerate is unique and quite unlike the non-deformable solid particles of earth materials and metal oxides because of the nature of the biological properties of these bimolecular materials. Most solid non-deformable particles such as earth materials or metal oxides have a density much higher than water. Therefore, once these small particles are flocculated, their particle size greatly increases, and the resulting flocs quickly settle (i.e., in minutes) by gravity. In contrast, cells, mAbs and other biomolecule species are made of amino acids and water, and have a density very close to the density of water. Therefore, flocculated cells and other biomolecules don't readily settle and often take a number of hours before settling occurs.

Another problem is the relatively low density of the flocculated cell mass which, typically form a fluffy mass that occupies significant part of the feed volume rather than forming a compacted cake. Also, because of the biological origin of the particles, the flocs are fragile and tend to break down easily under pressure.

For this reason, most conventional solid-liquid separation methods while useful for solid particle systems, fail in flocculated cell masses such as mAb feedstocks.

Particle retention is believed to involve both size exclusion and adsorption through hydrophobic, ionic and other interactions. Fouling mechanisms may include pore blockage, cake formation and/or pore constriction. Depth filters are advantageous because they are very effective in removing contaminants and come in disposable formats thereby eliminating validation and contamination issues related to re-usable hardware installations, such as those encountered when using a centrifuge. However, depth filters are currently unable to handle the high solids feedstreams that are typical of high titer mAb processes, such that depth filters are therefore often used after centrifuging. The high particulate load and high turbidity present in unclarified cell culture supernatant adds challenges to the primary clarification by depth filtration alone.

However, depth filters are currently unable to handle the primary clarification of high-solids feedstreams, and often must be used after centrifugation or tangential flow microfiltration. The high particulate load and high turbidity present in unclarified cell culture supernatant adds challenges to primary clarification by depth filtration alone. Currently, the limited throughput results in large installations of depth filters for primary clarification which results in yield losses due to the large hold up volume and scale-up issues as discussed above.

In addition, mAb feedstocks are challenging feed streams to clarify and filter because of the presence of a higher biomass content, and result in a high turbidity centrate after centrifugation. Because of the need to remove large amounts of biomass, the high turbidity centrates shorten the life of the depth filter for clarification downstream. A need exists improve the clarification of mAbs thereby resulting in higher throughputs.

In light of the above primary clarification processes which rely on the use of a primary clarification centrifugation step or a primary clarification microfiltration step followed by a secondary clarification step which relies on depth filtration media to remove larger particles, a need exists for a disposable, reasonably reliable, and not inordinately expensive to implement, primary clarification process that does not use a primary clarification centrifugation or microfiltration step followed by an additional secondary clarification step.

SUMMARY OF THE INVENTION

In response to the above needs and problems associated with the primary clarification processes of feeds, feedstreams, feedstocks, cell culture broths and the like, the present invention overcomes the challenges by using a primary clarification depth filtration process which utilizes a primary clarification depth filtration device without the use a primary clarification centrifugation step or primary clarification tangential flow microfiltration step.

The present invention encompasses a process for the primary clarification, by depth filtration, of feeds, feedstreams, feedstocks, cell culture broths and the like, containing a target biomolecule of interest and a plurality of cellular debris and colloidal particulates without the use of a primary clarification centrifugation step or a primary clarification tangential flow microfiltration step, the process comprising:

a) providing a depth filtration device having a porous depth filter media;

b) providing a feed stream containing a target biomolecule of interest and a plurality of cellular debris and particulates, wherein the cellular debris and particulates have a particle size distribution of about 0.5 μm to about 200 μm;

c) contacting the porous depth filter media with the feed stream, such that the depth filter media is capable of filtering cellular debris and particulates having a particle size distribution of about 0.5 μm to about 200 μm at a flow rate of about 10 litres/m²/hr to about 100 litres/m²/hr; and d) separating the target biomolecule of interest from the cellular debris and particulates without the use of a primary clarification centrifugation step or a primary clarification tangential flow microfiltration step.

The present invention further encompasses a process for the primary clarification by depth filtration of a flocculated feed containing therein a target biomolecule of interest or biotherapeutic of interest and flocculated cellular debris, materials, and colloidal particulates using a primary clarification depth filtration device without the use of a primary clarification centrifugation step or a primary clarification tangential flow microfiltration step, the process comprising:

a) providing a depth filtration device containing a porous depth filter media;

b) providing a chemical flocculant;

c) providing a feed containing a target biomolecule of interest and a plurality of cellular material, debris and colloidal particulates;

d) combining the chemical flocculant to the feed;

e) forming chemically flocculated cellular materials, debris and colloidal particulates in the feed, and optionally chemically flocculating the target biomolecule of interest;

f) contacting the porous depth filter media with the feed containing the chemically flocculated cellular materials, debris and colloidal particulates; and g) separating the flocculated bimolecular species of interest and the plurality of flocculated cellular material without the use of a centrifugation clarification step or a tangential flow microfiltration clarification step.

The present invention is directed towards the primary clarification of feed using depth filtration devices without the use of a primary clarification centrifugation step or primary clarification tangential flow microfiltration step. The depth filtration devices are able to filter high solids feeds containing particles having a particle size distribution of approximately 0.5 μm to 200 μm at a flow rate of about 10 litres/m²/hr to about 100 litres/m²/hr until the TMP reaches 20 psi. The primary clarification depth filter media taught herein include graded porous layers of varying pore ratings.

One preferred application of the primary clarification porous anisotropic depth filters media provided herein is the primary clarification of chemically treated flocculated high solids feeds containing a bimolecular species or biotherapeutic of interest, and a plurality of flocculated cellular debris and flocculated colloidal particulates.

In certain embodiments, the invention provides a process for using a depth filtration device having a porous filter media in the primary clarification of flocculated feeds containing mAbs, mammalian cell cultures, plant cell cultures, bacteria cell cultures, insect cell cultures, and other bimolecular cellular materials and cultures of interest, by efficiently separating flocculated aggregated cellular masses and debris from the biomolecular species of interest without the use of a primary clarification centrifugation step or a primary clarification tangential flow microfiltration step by using a fiber based porous depth filter media capable of performing depth filtration of a high volume of feedstock containing very large particles without the unintended effect of cake filtration.

In certain embodiments, the invention provides a depth filtration device including a porous depth filter media having multiple graded layers for use in primary clarification and the removal of aggregated cellular biomass, including flocculated cellular debris and colloidal particulates with a size larger than about 10 microns (μm) or smaller particles with the use of a flocculating agent.

In still other embodiments, the invention provides a depth filtration device including a porous depth filter media having open graded layers for use in primary clarification depth filtration that enables the depth filtration of cellular debris and colloidal particulates having particle sizes varying from 0.5 μm to 200 μm, thereby improving the throughput for the unclarified feedstreams without the unintended effect of cake filtration.

In certain embodiments, the present invention provides a depth filtration media:

a) having large pores for the large flocs of cellular debris to penetrate without the unintended effect of cake filtration or the formation of floc bridging inside the pores of the filter;

b) with very high depth to spread out the cell masses to prevent internal floc bridging, which would lead to internal cake filtration inside the media, external to or internal to the media in order to avoid concentration of the pressure drop which could cause floc breakdown;

c) having an anisotropic depth filter layer, i.e. with a gradual reduction in pore size that matches the population of the floc size in the feedstock. For certain feedstocks with significant amount of fine flocs such as those produced from acid flocculation instead of polymers, the depth filter layer includes a composite media having a combination of felt material, DE and chopped fibers for fine removal is needed;

d) for the primary clarification of bimolecular species of interest with mean particle sizes greater than 10 um, typical of flocculant and chemically treated feed streams where the depth filter includes graded layers of non-woven fibers with open nominal pore size ratings capable of filtering flocculated feed streams with high amount of solids;

e) of composite graded layers of non-woven fibers and cellulose/diamatoceous earth with open nominal pore size ratings capable of filtering polymer flocculant treated feed streams with high amount of solids;

f) having good retentive properties for the polymer flocculant (eg. smart polymer (SmP), chitosan etc) treated feeds despite the greater permeability;

g) having good retentive properties for the polymer flocculant (eg. acid precipitation, caprylic acid etc) treated feeds despite the greater permeability;

h) used in the process for primary clarification of cell and cell debris containing cultures using a depth filter comprising graded layers of non-woven fibers; and i) used in the process for primary clarification of flocculated cell and cell debris containing cultures using a depth filter comprising graded layers of non-woven fibers.

In certain embodiments, the invention provides a depth filtration media prefilter for depth filters having a nominal pore size<about 25 μm comprising graded layers of non-woven fibers.

In still other embodiments, the invention provides a depth filtration media prefilter for depth filters with a nominal pore size<25 about μm comprising at least three graded layers of non-woven fibers.

In still other embodiments, the invention provides a depth filtration media including a depth filter including at least two layers of graded non-woven fibers with a nominal pore size rating>about 25 μm capable of filtering flocculated feed streams with >about 3% solids.

In still other embodiments, the invention provides a depth filtration media including a depth filter including at least two layers graded non-woven fibers with a nominal pore size rating>about 25 μm capable of filtering polymer flocculated feed streams with >about 3% solids.

In still other embodiments, the invention provides a depth filtration media including a depth filters comprising of at least two layers of graded non-woven fibers with a nominal pore size rating>about 25 μm capable of filtering polymer flocculated feed streams with >about 3% solids resulting in a turbidity output<20 NTU.

To overcome the present challenges associated with the depth filters, the present invention is directed towards the development of a primary clarification depth filter media and process of using the same which can filter high solid containing fluid streams having a particle size distribution of approximately 0.5 microns to 200 microns at a flow rate of about 10 litres/m$^2$/hr (10 LMH) to 100 litres/m$^2$/hr (100 LMH) until the TMP reaches 20 psi. The primary clarification depth filter includes graded layers having various pore ratings with the application in primary clarification for polymer and chemically treated flocculated feeds.

The present invention is directed towards depth filters for disposable primary clarification processes. The use of open graded layers for depth filtration enables the filtration of feeds containing large clusters with the potential to eliminate centrifugation, and enables the filtration of higher solids having particle sizes varying from about 0.5 microns to about 200 microns, thereby improving the throughput for these unclarified feedstreams.

Additional features and advantages of the invention will be set forth in the detailed description and claims, which follows. Many modifications and variations of this invention can be made without departing from its spirit and scope, as will be apparent to those skilled in the art. It is to be understood that the foregoing general description and the following detailed description, the claims, as well as the appended drawings are exemplary and explanatory only, and are intended to provide an explanation of various embodiments of the present teachings. The specific embodiments described herein are offered by way of example only and are not meant to be limiting in any way.

BRIEF DESCRIPTION OF THE DRAWINGS

The accompanying drawings, which are incorporated in and constitute a part of this specification, illustrate the presently contemplated embodiments of the invention and, together with the description, serve to explain the principles of the invention.

FIGS. 1B, 1D and 1F depict primary clarification depth filters having at least eight layers for use with chemically treated feeds (acid treatment)

DESCRIPTION OF THE EMBODIMENTS

Figure 1A:
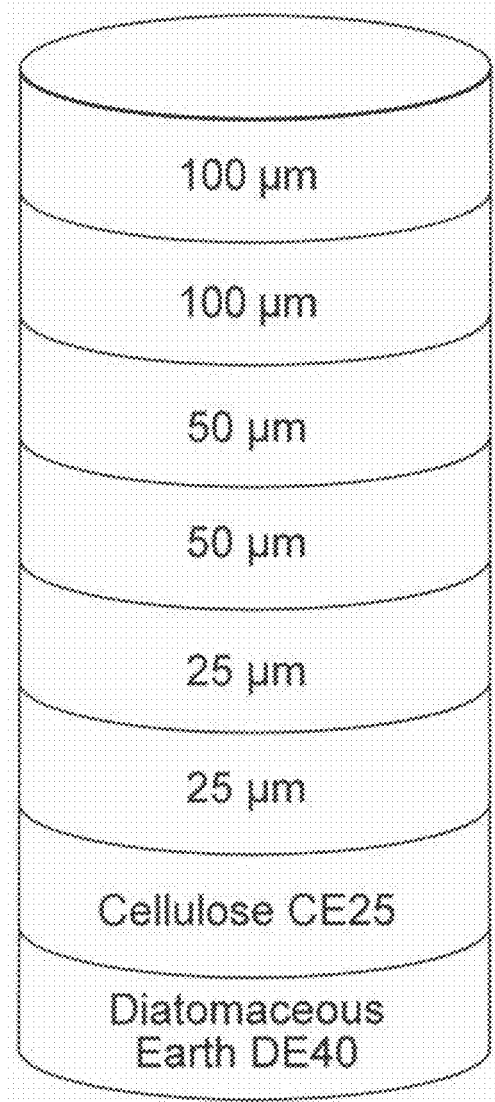
FIGS. 1A, 1B, 1C, 1D, 1E, and 1F depict different schematic embodiments of examples of primary clarification depth filters according to the invention, wherein FIG. 1A (eight layers), FIG. 1C (seven layers) and FIG. 1E (eight layers) depict primary clarification depth filters for use with polymer flocculant (smart polymer) treated feeds.

All publications, patents and patent applications cited herein, whether supra or infra, are hereby incorporated by reference in their entirety to the same extent as if each individual publication, patent or patent application was specifically and individually indicated to be incorporated by reference.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about" whether or not explicitly indicated. The term "about" generally refers to a range of numbers that one would consider equivalent to the recited value (i.e., having the same function or result). In many instances, the term "about" may include numbers that are rounded to the nearest significant figure.

Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Before describing the present invention in further detail, a number of terms will be defined. Use of these terms does not limit the scope of the invention but only serve to facilitate the description of the invention.

Unless defined otherwise, all technical and scientific terms used herein have the same meaning as commonly understood by one of ordinary skill in the art to which this invention is related. The following terms are defined for purposes of the invention as described herein.

As used herein, the singular forms "a," "an," and "the" include plural referents unless the context clearly dictates otherwise.

The term "bioreactor," as used herein, refers to any manufactured or engineered device or system that supports a biologically active environment. In some instances, a bioreactor is a vessel in which a cell culture process is carried out which involves organisms or biochemically active substances derived from such organisms. Such a process may be either aerobic or anaerobic. Commonly used bioreactors are typically cylindrical, ranging in size from liters to cubic meters, and are often made of stainless steel. In some embodiments described herein, a bioreactor is made of a material other than steel and is disposable or single-use. It is contemplated that the total volume of a bioreactor may be any volume ranging from 100 mL to up to 10,000 Liters or more, depending on a particular process. In some embodiments according to the processes and systems described herein, the bioreactor is connected to a unit operation such as a depth filter. In some embodiments described herein, a bioreactor is used for both cell culturing as well as for precipitation, where a precipitant may be added directly to a bioreactor, thereby to precipitate one or more impurities.

The term "cell culture," refers to cells grown in suspension, roller bottles, flasks and the like, as well as the components of the suspension itself, including but not limited to cells, cell debris, cellular contaminants, colloidal particles, biomolecules, HCP, host cell proteins (HCP) and DNA, mAbs, flocculants. Large scale approaches, such as bioreactors, including adherent cells growing attached to microcarriers in stirred fermentors, are also encompassed by the term "cell culture." Moreover, it is possible to not only to culture contact-dependent cells, but also to use the suspension culture techniques in the methods of the claimed invention. Exemplary microcarriers include, for example, dextran, collagen, plastic, gelatin and cellulose and others as described in Butler, Spier & Griffiths, Animal cell Biotechnology 3:283-303 (1988). Porous carriers, such as, for example, Cytoline® or Cytopore®, as well as dextran-based carriers, such as DEAE-dextran (Cytodex 1®), quaternary amine-coated dextran (Cytodex 2®) or gelatin-based carriers, such as gelatin-coated dextran (Cytodex 3®) may also be used. Cell culture procedures for both large and small-scale production of proteins are encompassed by the present invention. Procedures including, but not limited to, a fluidized bed bioreactor, hollow fiber bioreactor, roller bottle culture, or stirred tank bioreactor system may be used, with or without microcarriers, and operated alternatively in a batch, fed-batch, or perfusion mode.

The terms "cell culture medium," and "culture medium" refer to a nutrient solution used for growing animal cells, e.g., mammalian cells. Such a nutrient solution generally includes various factors necessary for cell attachment, growth, and maintenance of the cellular environment. For example, a typical nutrient solution may include a basal media formulation, various supplements depending on the cell type and, occasionally, antibiotics. In some embodiments, a nutrient solution may include at least one component from one or more of the following categories: 1) an energy source, usually in the form of a carbohydrate such as glucose; 2) all essential amino acids, and usually the basic set of twenty amino acids plus cystine; 3) vitamins and/or other organic compounds required at low concentrations; 4) free fatty acids; and 5) trace elements, where trace elements are defined as inorganic compounds or naturally occurring elements that are typically required at very low concentrations, usually in the micromolar range. The nutrient solution may optionally be supplemented with one or more components from any of the following categories: 1) hormones and other growth factors as, for example, insulin, transferrin, and epidermal growth factor; 2) salts and buffers as, for example, calcium, magnesium, and phosphate; 3) nucleosides and bases such as, for example, adenosine and thymidine, hypoxanthine; and 4) protein and tissue hydrolysates. In general, any suitable cell culture medium may be used. The medium may be comprised of serum, e.g. fetal bovine serum, calf serum or the like. Alternatively, the medium may be serum free, animal free, or protein free.

The term "cell culture additive," as used herein, refers to a molecule (e.g., a non-protein additive), which is added to a cell culture process in order to facilitate or improve the cell culture or fermentation process. In some embodiments according to the present invention, a stimulus responsive polymer, as described herein, binds and precipitates one or more cell culture additives. Exemplary cell culture additives include anti-foam agents, antibiotics, dyes and nutrients.

The terms "Chinese hamster ovary cell protein" and "CHOP," as used interchangeably herein, refer to a mixture of host cell proteins ("HCP") derived from a Chinese hamster ovary ("CHO") cell culture. The HCP or CHOP is generally present as an impurity in a cell culture medium or lysate (e.g., a harvested cell culture fluid containing a protein or polypeptide of interest (e.g., an antibody or immunoadhesin expressed in a CHO cell). Generally, the amount of CHOP present in a mixture comprising a protein of interest provides a measure of the degree of purity for the protein of interest. Typically, the amount of CHOP in a protein mixture is expressed in parts per million relative to the amount of the protein of interest in the mixture. It is understood that where the host cell is another mammalian cell type, an *E. coli*, a yeast cell, an insect cell, or a plant cell, HCP refers to the proteins, other than target protein, found in a lysate of the host cell.

The terms "contaminant," "impurity," and "debris," as used interchangeably herein, refer to any foreign or objectionable material, including a biological macromolecule such as a DNA, an RNA, one or more host cell proteins (HCPs or CHOPs), endotoxins, viruses, lipids and one or more additives which may be present in a sample containing a protein or polypeptide of interest (e.g., an antibody) being separated from one or more of the foreign or objectionable molecules using a stimulus responsive polymer according to the present invention. In some embodiments, a stimulus responsive polymer described herein binds and precipitates a protein or polypeptide of interest from a sample containing the protein or polypeptide of interest and one or more impurities. In other embodiments, a stimulus responsive polymer described herein binds and precipitates one or more impurities, thereby to separate the polypeptide or protein of interest from one or more impurities.

The term "surge tank" as used herein refers to any container or vessel or bag, which is used between process steps or within a process step (e.g., when a single process step comprises more than one step); where the output from one step flows through the surge tank onto the next step.

Accordingly, a surge tank is different from a pool tank, in that it is not intended to hold or collect the entire volume of output from a step; but instead enables continuous flow of output from one step to the next. In some embodiments, the volume of a surge tank used between two process steps or within a process step in a process or system described herein, is no more than 25% of the entire volume of the output from the process step. In another embodiment, the volume of a surge tank is no more than 10% of the entire volume of the output from a process step. In some other embodiments, the volume of a surge tank is less than 35%, or less than 30%, or less than 25%, or less than 20%, or less than 15%, or less than 10% of the entire volume of a cell culture in a bioreactor, which constitutes the starting material from which a target molecule is to be purified.

The term "static mixer" refers to a device for mixing two fluid materials, typically liquids. The device generally consists of mixer elements contained in a cylindrical (tube) housing. The overall system design incorporates a method for delivering two streams of fluids into the static mixer. As the streams move through the mixer, the non-moving elements continuously blend the materials. Complete mixing depends on many variables including the properties of the fluids, inner diameter of the tube, number of mixer elements and their design etc.

As used herein the term "depth filter" (e.g., gradient-density depth filter) achieves filtration within the depth of the filter material. A common class of such filters are those that comprise a random matrix of fibers bonded (or otherwise fixed), to form a complex, tortuous maze of flow channels. Particle separation in these filters generally results from entrapment by or adsorption to, the fiber matrix. The most frequently used depth filter media for bioprocessing of cell culture broths and other feedstocks consists of cellulose fibers, a filter aid such as DE, and a positively charged resin binder. Depth filter media, unlike absolute filters, retain particles throughout the porous media allowing for retention of particles both larger and smaller than the pore size. Particle retention is thought to involve both size exclusion and adsorption through hydrophobic, ionic and other interactions. The fouling mechanism may include pore blockage, cake formation and/or pore constriction. Depth filters are advantageous because they remove contaminants and also come in disposable formats thereby eliminating the validation issues.

The term "affinity chromatography matrix," as used herein, refers to a chromatography matrix which carries ligands suitable for affinity chromatography. Typically the ligand (e.g., Protein A or a functional variant or fragment thereof) is covalently attached to a chromatography matrix material and is accessible to the target molecule in solution as the solution contacts the chromatography matrix. One example of an affinity chromatography matrix is a ProteinA matrix. An affinity chromatography matrix typically binds the target molecules with high specificity based on a lock/key mechanism such as antigen/antibody or enzyme/receptor binding. Examples of affinity matrices are matrices carrying protein A ligands like Protein A SEPHAROSE™ or PROSEP®-A. In the processes and systems described herein, an affinity chromatography step may be used as the bind and elute chromatography step in the entire purification process.

The terms "ion-exchange" and "ion-exchange chromatography," as used herein, refer to the chromatographic process in which a solute or analyte of interest (e.g., a target molecule being purified) in a mixt mixture, interacts with a charged compound linked (such as by covalent attachment) to a solid phase ion exchange material, such that the solute or analyte of interest interacts non-specifically with the charged compound more or less than solute impurities or contaminants in the mixture. The contaminating solutes in the mixture elute from a column of the ion exchange material faster or slower than the solute of interest or are bound to or excluded from the resin relative to the solute of interest.

"Ion-exchange chromatography" specifically includes cation exchange, anion exchange, and mixed mode ion exchange chromatography. For example, cation exchange chromatography can bind the target molecule (e.g., an Fc region containing target protein) followed by elution (e.g., using cation exchange bind and elute chromatography or "CIEX") or can predominately bind the impurities while the target molecule "flows through" the column (cation exchange flow through chromatography FT-CIEX). Anion exchange chromatography can bind the target molecule (e.g., an Fc region containing target protein) followed by elution or can predominately bind the impurities while the target molecule "flows through" the column, also referred to as negative chromatography. In some embodiments and as demonstrated in the Examples set forth herein, the anion exchange chromatography step is performed in a flow through mode.

The term "ion exchange matrix" refers to a matrix that is negatively charged (i.e., a cation exchange media) or positively charged (i.e., an anion exchange media). The charge may be provided by attaching one or more charged ligands to the matrix, e.g., by covalent linkage. Alternatively, or in addition, the charge may be an inherent property of the matrix (e.g., as is the case of silica, which has an overall negative charge).

The term "anion exchange matrix" is used herein to refer to a matrix which is positively charged, e.g. having one or more positively charged ligands, such as quaternary amino groups, attached thereto. Commercially available anion exchange resins include DEAE cellulose, QAE SEPHADEX™ and FAST Q SEPHAROSE™ (GE Healthcare). Other exemplary materials that may be used in the processes and systems described herein are Fractogel® EMD TMAE, Fractogel® EMD TMAE highcap, Eshmuno® Q and Fractogel® EMD DEAE (EMD Millipore).

The term "cation exchange matrix" refers to a matrix which is negatively charged, and which has free cations for exchange with cations in an aqueous solution contacted with the solid phase of the matrix. A negatively charged ligand attached to the solid phase to form the cation exchange matrix or resin may, for example, be a carboxylate or sulfonate. Commercially available cation exchange matrices include carboxy-methyl-cellulose, sulphopropyl (SP) immobilized on agarose (e.g., SP-SEPHAROSE FAST FLOW™ or SP-SEPHAROSE HIGH PERFORMANCE™, from GE Healthcare) and sulphonyl immobilized on agarose (e.g. S-SEPHAROSE FAST FLOW™ from GE Healthcare). Preferred is Fractogel® EMD SO$_3$, Fractogel® EMD SE Highcap, Eshmuno® S and Fractogel® EMD COO (EMD Millipore).

The term "impurity" or "contaminant" as used herein, refers to any foreign or objectionable molecule, including a biological macromolecule such as DNA, RNA, one or more host cell proteins, endotoxins, lipids and one or more additives which may be present in a sample containing the target molecule that is being separated from one or more of the foreign or objectionable molecules using a process of the present invention. Additionally, such impurity may include any reagent which is used in a step which may occur prior to the method of the invention. An impurity may be soluble or insoluble in nature.

The term "insoluble impurity," as used herein, refers to any undesirable or objectionable entity present in a sample containing a target molecule, where the entity is a suspended particle or a solid. Exemplary insoluble impurities include whole cells, cell fragments and cell debris.

The term "soluble impurity," as used herein, refers to any undesirable or objectionable entity present in a sample containing a target molecule, where the entity is not an insoluble impurity. Exemplary soluble impurities include host cell proteins (HCPs), DNA, RNA, viruses, endotoxins, cell culture media components, lipids etc.

The term "continuous process," as used herein, refers to a process for purifying a target molecule, which includes two or more process steps (or unit operations), such that the output from one process step flows directly into the next process step in the process, without interruption, and where two or more process steps can be performed concurrently for at least a portion of their duration. In other words, in case of a continuous process, as described herein, it is not necessary to complete a process step before the next process step is started, but a portion of the sample is always moving through the process steps. The term "continuous process" also applies to steps within a process step, in which case, during the performance of a process step including multiple steps, the sample flows continuously through the multiple steps that are necessary to perform the process step. One example of such a process step described herein is the flow through purification step which includes multiple steps that are performed in a continuous manner, e.g., flow-through activated carbon followed by flow-through AEX media followed by flow-through CEX media followed by flow-through virus filtration.

In some embodiments, a depth filter, as described herein, is used for clarification, following which the clarified cell culture can continuously flow onto the next step in the purification process, e.g., a bind and elute chromatography step (e.g., Protein A affinity chromatography).

The term "semi-continuous process," as used herein, refers to a generally continuous process for purifying a target molecule, where input of the fluid material in any single process step or the output is discontinuous or intermittent. For example, in some embodiments according to the present invention, the input in a process step (e.g., a bind and elute chromatography step) may be loaded continuously; however, the output may be collected intermittently, where the other process steps in the purification process are continuous. Accordingly, in some embodiments, the processes and systems described herein are "semi-continuous" in nature, in that they include at least one unit operation which is operated in an intermittent matter, whereas the other unit operations in the process or system may be operated in a continuous manner.

The term "connected process" refers to a process for purifying a target molecule, where the process comprises two or more process steps (or unit operations), which are in direct fluid communication with each other, such that fluid material continuously flows through the process step in the process and is in simultaneous contact with two or more process steps during the normal operation of the process. It is understood that at times, at least one process step in the process may be temporarily isolated from the other process steps by a barrier such as a valve in the closed position. This temporary isolation of individual process steps may be necessary, for example, during start up or shut down of the process or during removal/replacement of individual unit operations. The term "connected process" also applies to steps within a process step, e.g., when a process step requires several steps to be performed in order to achieve the intended result of the process step. One such example is the flow-through purification process step, as described herein, which may include several steps to be performed in a flow-through mode, e.g., activated carbon; anion exchange chromatography, cation exchange chromatography and virus filtration.

The term "fluid communication," as used herein, refers to the flow of fluid material between two process steps or flow of fluid material between steps of a process step, where the process steps are connected by any suitable means (e.g., a connecting line or surge tank), thereby to enable the flow of fluid from one process step to another process step. In some embodiments, a connecting line between two unit operations may be interrupted by one or more valves to control the flow of fluid through the connecting line.

The terms "purifying," "purification," "separate," "separating," "separation," "isolate," "isolating," or "isolation," as used herein, refer to increasing the degree of purity of a target molecule from a sample comprising the target molecule and one or more impurities. Typically, the degree of purity of the target molecule is increased by removing (completely or partially) at least one impurity from the sample.

The term "precipitate," precipitating" or "precipitation" as used herein, refers to process used in clarification, in which the properties of the undesirable impurities are modified such that they can be more easily separated from the soluble target molecule. This is typically accomplished by forming large aggregate particles and/or insoluble complexes containing the undesirable impurities. These particles have properties (e.g. density or size) such that they can be more easily separated from the liquid phase that contains the soluble target molecule, such as by filtration or centrifugation. In some cases, a phase change is effected, such that the undesirable impurities can be more easily separated from the soluble target molecule. Precipitation by phase change can be effected by the addition of a precipitating agent, such as a polymer or a small molecule. In a particular embodiment, the precipitant is a stimulus responsive polymer, also referred to as a smart polymer. In some embodiments described herein, the precipitant or precipitating agent is a flocculant. Flocculation, as used herein, is one way of performing precipitation where the performance typically depends on the flocculant concentration used ("dose dependent"). Typical flocculating agents are polyelectrolytes, such as polycations, that complex with oppositely charged impurities.

In some embodiments described herein, clarification employs the addition of a precipitant to a sample containing a target molecule and one or more impurities followed by depth filtration. In some cases, a change in solution conditions (such as temperature, pH, salinity) may be used to initiate the precipitation, such as in the case of stimulus responsive polymers. The precipitated material which contains the one or more impurities as well as the precipitating agent is removed thereby recovering the target molecule in the liquid phase, where the liquid is then typically subjected to further process steps in order to further purify the target molecule.

Precipitation may be performed directly in a bioreactor containing a cell culture expressing a target molecule to be purified, where a precipitant is added directly to the bioreactor. Alternatively, the precipitant may be added to the cell culture, which typically contains the target molecule, in a separate vessel.

There are many ways known to those skilled in the art of removing the precipitated material, such as filtration or settling or any combinations thereof.

The term "settling," as used herein, refers to a sedimentation process in which the precipitated material migrates to the bottom of a vessel under the influence of gravitational forces. Settling can be followed by decanting or filtering of the liquid phase or supernatant.

As used herein the term "smart polymer" (SmP), (also known as stimuli-responsive polymers or intelligent polymers or Affinity Macro Ligands (AML)), as used herein means a group of polymers that are biologically, chemically, or physically responsive to an external stimulus such as to changes in environmental conditions such pH, temperature, light, ionic strength, radiation, voltage, external pressure, solvent composition, or other stimulus. Smart polymers respond with large property changes to small physical or chemical stimuli, and can reversibly change their physical or chemical properties in response to these environmental stimuli (Roy and Gupta, 2003; Kopecek, 2007). Smart polymers can take many forms; they may be dissolved in an aqueous solution, adsorbed or grafted on aqueous-solid interfaces, or cross-linked to form hydrogels [Hoffman J Controlled Release (1987) 6:297-305; Hoffman Intelligent polymers. In: Park K, ed. Controlled drug delivery. Washington: ACS Publications, (1997) 485-98; Hoffman Intelligent polymers in medicine and biotechnology. Artif Organs (1995) 19:458-467]. Typically, when the polymer's critical response is stimulated, the smart polymer in solution will show a sudden onset of turbidity as it phase-separates; the surface-adsorbed or grafted smart polymer will collapse, converting the interface from hydrophilic to hydrophobic; and the smart polymer (cross-linked in the form of a hydrogel) will exhibit a sharp collapse and release much of its swelling solution. Smart polymers may be physically mixed with, or chemically conjugated to, biomolecules to yield a large family of polymer-biomolecule systems that can respond to biological as well as to physical and chemical stimuli. Biomolecules that may be polymer-conjugated include proteins and oligopeptides, sugars and polysaccharides, single- and double-stranded oligonucleotides and DNA plasm ids, simple lipids and phospholipids, and a wide spectrum of recognition ligands and synthetic drug molecules. A number of structural parameters control the ability of smart polymers to specifically precipitate proteins of interest; smart polymers should contain reactive groups for ligand coupling; not interact strongly with the impurities; make the ligand available for interaction with the target protein; and form compact precipitates.

As used herein the phrase "high solids" containing feed, means a feed having approximately >7% solids, while the phrase "low solid" containing feeds would be approximately 0.1%-7% solids.

The term "stimulus" or "stimuli," as used interchangeably herein, is meant to refer to a physical or chemical change in the environment which results in a response by a stimulus responsive polymer according to the present invention. Accordingly, the present invention provides novel polymers which are responsive to a stimulus and which stimulus results in a change in the solubility of the polymer. Examples of stimuli to which one or more polymers described herein are responsive, include, but are not limited to, e.g., changes in temperature, changes in conductivity and/or changes in pH. In some embodiments, a stimulus comprises addition of a complexing agent or a complex forming salt to a sample. In various embodiments, a stimulus is generally added after the addition of a polymer to a sample. Although, the stimulus may also be added during or before addition of a polymer to a sample.

The term "polymer" as used herein, refers to a molecule formed by covalent linkage of two or more monomer units. These monomer units can be synthetic or occur in nature. The polymers formed by the repeating units can be linear or branched. Examples of polymers include, but are not limited to, polyethylene glycol, polypropylene glycol, polyethylene, polyallylamine, polyvinylalcohol, polystyrene and copolymers (e.g. polystyrene-co-polypyridine, polyacrylic acid-co-methyl methacrylate, pluronics, PF68 etc). In some embodiments according to the present invention, polymers comprise a polyelectrolyte backbone.

The terms "Protein A" and "Prot A" are used interchangeably herein and encompasses Protein A recovered from a native source thereof, Protein A produced synthetically (e.g., by peptide synthesis or by recombinant techniques), and variants thereof which retain the ability to bind proteins which have a $CH_2/CH_3$ region, such as an Fc region. Protein A can be purchased commercially from Repligen, GE or Fermatech. Protein A is generally immobilized on a chromatography matrix. A functional derivative, fragment or variant of Protein A used in the methods and systems according to the present invention may be characterized by a binding constant of at least $K=10^8$ M, and preferably $K=10^9$ M, for the Fc region of mouse IgG2a or human IgG1. An interaction compliant with such value for the binding constant is termed "high affinity binding" in the present context. In some embodiments, such functional derivative or variant of Protein A comprises at least part of a functional IgG binding domain of wild-type Protein A, selected from the natural domains E, D, A, B, C or engineered mutants thereof which have retained IgG binding functionality.

Also, Protein A derivatives or variants engineered to allow a single-point attachment to a solid support may also be used in the affinity chromatography step in the claimed methods.

Single point attachment generally means that the protein moiety is attached via a single covalent bond to a chromatographic support material of the Protein A affinity chromatography. Such single-point attachment may also occur by use of suitably reactive residues which are placed at an exposed amino acid position, namely in a loop, close to the N- or C-terminus or elsewhere on the outer circumference of the protein fold. Suitable reactive groups are e.g. sulfhydryl or amino functions.

In some embodiments, Protein A derivatives of variants are attached via multi-point attachment to suitable a chromatography matrix.

The term "affinity chromatography matrix," as used herein, refers to a chromatography matrix which carries ligands suitable for affinity chromatography. Typically the ligand (e.g., Protein A or a functional variant or fragment thereof) is covalently attached to a chromatography matrix material and is accessible to the target molecule in solution as the solution contacts the chromatography matrix. One example of an affinity chromatography matrix is a ProteinA matrix. An affinity chromatography matrix typically binds the target molecules with high specificity based on a lock/key mechanism such as antigen/antibody or enzyme/receptor binding. Examples of affinity matrices are matrices carrying protein A ligands like Protein A SEPHAROSE™ or PROSEP®-A. In the processes and systems described herein, an affinity chromatography step may be used as the bind and elute chromatography step in the entire purification process.

The term "stimulus responsive polymer," as used herein, is a polymer which exhibits a change in a physical and/or chemical property after the addition of a stimulus. A typical stimulus response is a change in the polymer's solubility. For example, the polymer poly(N-isopropylacrylamide) is water soluble at temperatures below about 35° C., but become insoluble in water at temperatures of about 35° C.

The term "flocculation," as used herein, refers to the addition of a flocculant, such as a polymer or chemically treated (e.g., acid treatment) described herein, to a solution in order to remove one or more suspended insoluble or soluble impurities. The polymer must be added to the solution at a concentration which allows for spontaneous formation of insoluble aggregates which can be removed from solution via typical solid-liquid separation methods.

The term "composition," "solution" or "sample," as used herein, refers to a mixture of a target molecule or a desired product to be purified using one or more stimulus responsive polymers or chemically treated (e.g., acid treatment) described herein along with one or more undesirable entities or impurities. In some embodiments, the sample comprises feedstock or cell culture media into which a target molecule or a desired product is secreted. In some embodiments, the sample comprises a target molecule (e.g., a therapeutic protein or an antibody) along with one or more impurities (e.g., host cell proteins, DNA, RNA, lipids, cell culture additives, cells and cellular debris). In some embodiments, the sample comprises a target molecule of interest which is secreted into the cell culture media.

In some embodiments, a sample from which a target molecule is to be purified using one or more stimulus responsive polymers or chemically treated (e.g., acid treatment) described herein is "partially purified" prior to contacting the sample with a stimulus responsive polymer. Partial purification may be accomplished, for example, by subjecting the sample to one or more purification steps, such as, e.g., one or more non-affinity chromatography steps. The target molecule may be separated from one or more undesirable entities or impurities either by precipitating the one or more impurities or by precipitating the target molecule.

The term "precipitate," precipitating" or "precipitation," as used herein, refers to the alteration of a bound (e.g., in a complex with a biomolecule of interest) or unbound polymer or other soluble species from an aqueous and/or soluble state to a non-aqueous and/or insoluble state.

The term "biomolecule of interest," as used herein, can be a desired target molecule such as, for example, a desired product or polypeptide of interest (e.g., an antibody), or it can be an undesirable entity, which needs to be removed from a sample containing the desired target molecule. Such undesirable entities include but are not limited to, for example, one or more impurities selected from host cell protein, DNA, RNA, protein aggregates, cell culture additives, viruses, endotoxins, whole cells and cellular debris. In addition, the biomolecule of interest may also be bound and precipitated by a stimulus responsive polymer or chemically treated (e.g., acid treatment) as described herein.

The terms "target molecule", "target biomolecule", "desired target molecule" and "desired target biomolecule," as used interchangeable herein, generally refer to a polypeptide or product of interest, which is desired to be purified or separated from one or more undesirable entities, e.g., one or more impurities, which may be present in a sample containing the polypeptide or product of interest.

The terms "protein of interest," "target polypeptide," "polypeptide of interest," and "target protein," as used interchangeably herein, generally refer to a therapeutic protein or polypeptide, including but not limited to, an antibody that is to be purified using a stimulus responsive polymer according to the present invention.

As used herein interchangeably, the term "polypeptide" or "protein," generally refers to peptides and proteins having more than about ten amino acids. In some embodiments, a stimulus responsive polymer described herein is used to separate a protein or polypeptide from one or more undesirable entities present in a sample along with the protein or polypeptide. In some embodiments, the one or more entities are one or more impurities which may be present in a sample along with the protein or polypeptide being purified. As discussed, above, in some embodiments, a stimulus responsive polymer described herein specifically binds and precipitates a protein or polypeptide of interest upon the addition of a stimulus to the sample. In other embodiments, a stimulus responsive polymer described herein binds to and precipitates an entity other than the protein or polypeptide of interest such as, for example, host cell proteins, DNA, viruses, whole cells, cellular debris and cell culture additives, upon the addition of a stimulus.

In some embodiments, a protein or polypeptide being purified using a stimulus responsive polymer described herein is a mammalian protein, e.g., a therapeutic protein or a protein which may be used in therapy. Exemplary proteins include, but are not limited to, for example, renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors; anti-clotting factors; atrial natriuretic factor; lung surfactant; a plasminogen activator; bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; Dnase; IgE; a cytotoxic T-lymphocyte associated antigen (CTLA), such as CTLA-4; inhibin; activin; vascular endothelial growth factor (VEGF); receptors for hormones or growth factors; Protein A or D; rheumatoid factors; a neurotrophic factor, neurotrophin-3, -4, -5, or -6 (NT-3, NT-4, NT-5, or NT-6), or a nerve growth factor such as NGF-β.; platelet-derived growth factor (PDGF); fibroblast growth factor; epidermal growth factor (EGF); transforming growth factor (TGF); insulin-like growth factor-I and -II (IGF-I and IGF-II); des(1-3)-IGF-1 (brain IGF-1), insulin-like growth factor binding proteins (IGFBPs); CD proteins; erythropoietin; osteoinductive factors; immunotoxins; a bone morphogenetic protein (BMP); an interferon; interleukins (Ils), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins; a tumor associated antigen such as HER2, HER3 or HER4 receptor; and fragments and/or variants of any of the above-listed polypeptides.

Further, in some embodiments, a protein or polypeptide purified using a smart polymer according to the present invention is an antibody, functional fragment or variant thereof. In some embodiments, a protein of interest is a recombinant protein containing an Fc region of an immunoglobulin.

The term "immunoglobulin," "Ig" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of antibody light chains are referred to interchangeably as "light chain constant regions", "light chain constant domains", "CL" regions or "CL" domains. The "constant" domains of antibody heavy chains are referred to interchangeably as "heavy chain constant regions", "heavy chain constant domains", "CH" regions or "CH" domains. The "variable" domains of antibody light chains are referred to interchangeably as "light chain variable regions", "light chain variable domains", "VL" regions or "VL" domains. The "variable" domains of antibody heavy chains are referred to interchangeably as "heavy chain variable regions", "heavy chain variable domains", "VH" regions or "VH" domains.

Immunoglobulins or antibodies may be monoclonal or polyclonal and may exist in monomeric or polymeric form, for example, IgM antibodies which exist in pentameric form and/or IgA antibodies which exist in monomeric, dimeric or multimeric form. Immunoglobulins or antibodies may also include multispecific antibodies (e.g., bispecific antibodies), and antibody fragments so long as they retain, or are modified to comprise, a ligand-specific binding domain. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. When produced recombinantly, fragments may be expressed alone or as part of a larger protein called a fusion protein. Exemplary fragments include Fab, Fab', F(ab')2, Fc and/or Fv fragments. Exemplary fusion proteins include Fc fusion proteins.

Generally, an immunoglobulin or antibody is directed against an "antigen" of interest. Preferably, the antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated. Where the antigen is a polypeptide, it may be a transmembrane molecule (e.g. receptor) or a ligand such as a growth factor.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). "Monoclonal antibodies" may also be isolated from phage antibody libraries using the techniques described in Clackson et al., Nature 352:624-628 (1991) and Marks et al., J. Mol. Biol. 222:581-597 (1991), for example.

Monoclonal antibodies may further include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Framework" or "FR" residues are those variable domain residues other than the hypervariable region residues as herein defined.

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence.

The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

In some embodiments, an antibody which is separated or purified using a stimulus responsive polymer according to the present invention is a therapeutic antibody. Exemplary therapeutic antibodies include, for example, trastuzumab (HERCEPTIN™, Genentech, Inc., Carter et al (1992) Proc. Natl. Acad. Sci. USA, 89:4285-4289; U.S. Pat. No. 5,725,856); anti-CD20 antibodies such as chimeric anti-CD20 "C2B8" U.S. Pat. No. 5,736,137; anti-IgE (Presta et al (1993) J. Immunol. 151:2623-2632; WO 95/19181); anti-CD18 (U.S. Pat. No. 5,622,700; WO 97/26912); anti-IgE, including E25, E26 and E27 (U.S. Pat. Nos. 5,714,338; 5,091,313; WO 93/04173; U.S. Pat. No. 5,714,338); anti-Apo-2 receptor antibody (WO 98/51793); anti-TNF-alpha antibodies including cA2 (REMICADE™), CDP571 and MAK-195 (U.S. Pat. No. 5,672,347; Lorenz et al (1996) J. Immunol. 156(4):1646-1653; Dhainaut et al (1995) Crit. Care Med. 23(9):1461-1469); anti-Tissue Factor (TF) (EP 0 420 937 B1); anti-CD4 antibodies such as the cM-7412 antibody (Choy et al (1996) Arthritis Rheum 39(1):52-56); anti-Fc receptor antibodies such as the M22 antibody directed against Fc gamma RI as in Graziano et al (1995) J. Immunol. 155(10):4996-5002; anti-GpIIb/IIIa antibodies; anti-RSV antibodies such as MEDI-493 (SYNAGIS™); anti-CMV antibodies such as PROTOVIR™); anti-HIV antibodies such as PRO542; anti-hepatitis antibodies such as the anti-Hep B antibody OSTAVIR™); anti-CA 125 antibody OvaRex; anti-idiotypic GD3 epitope antibody BEC2; anti-alpha v beta3 antibody VITAXIN™ anti-human renal cell carcinoma antibody such as ch-G250; ING-1; anti-human 17-1A antibody (3622W94); and anti-human leukocyte antigen (HLA) antibodies such as Smart ID10 and the anti-HLA DR antibody Oncolym (Lym-1).

The terms "isolating," "purifying" and "separating," are used interchangeably herein, in the context of purifying a target molecule (e.g., a polypeptide or protein of interest) from a composition or sample comprising the target molecule and one or more impurities, using a stimulus responsive polymer described herein. In some embodiments, the degree of purity of the target molecule in a sample is increased by removing (completely or partially) one or more impurities from the sample by using a stimulus responsive polymer, as described herein. In another embodiment, the degree of purity of the target molecule in a sample is increased by precipitating the target molecule away from one or more impurities in the sample.

In some embodiments, a purification process additionally employs one or more "chromatography steps." Typically, these steps may be carried out, if necessary, after the separation of a target molecule from one or more undesired entities using a stimulus responsive polymer according to the present invention.

In some embodiments, a "purification step" to isolate, separate or purify a polypeptide or protein of interest using a stimulus responsive polymer described herein, may be part of an overall purification process resulting in a "homogeneous" or "pure" composition or sample, which term is used herein to refer to a composition or sample comprising less than 100 ppm HCP in a composition comprising the protein of interest, alternatively less than 90 ppm, less than 80 ppm, less than 70 ppm, less than 60 ppm, less than 50 ppm, less than 40 ppm, less than 30 ppm, less than 20 ppm, less than 10 ppm, less than 5 ppm, or less than 3 ppm of HCP. As used herein "primary clarification" includes the removal of aggregated cellular biomass, including flocculated cellular debris and colloidal particulates with a size larger than about 10 microns (µm) or smaller particles with the use of a flocculating agent.

The terms "clarify", "clarification", "clarification step," as used herein, generally refers to one or more steps used initially in the purification of biomolecules. The clarification step generally comprises removal of cells and/or cellular debris using one or more steps including any of the following alone or various combinations thereof, e.g., clarification depth filtration, precipitation, flocculation and settling. In some embodiments, the present invention provides an improvement over the conventional clarification step commonly used in various purification schemes. Clarification steps generally involve the removal of one or more undesirable entities and is typically performed prior to a step involving capture of the desired target molecule. Another key aspect of clarification is the removal of soluble and insoluble components in a sample which may later on result in the fouling of a sterile filter in a purification process, thereby making the overall purification process more economical. Furthermore, methods for enhancing clarification efficiency can be used, e.g. precipitation. Precipitation of impurities can be performed by various means such as by flocculation, pH adjustment (acid precipitation), temperature shifts, phase change due to stimulus-responsive polymers or small molecules, or any combinations of these methods.

The term "chromatography," as used herein, refers to any kind of technique which separates an analyte of interest (e.g., a target molecule) from other molecules present in a mixture. Usually, the analyte of interest is separated from other molecules as a result of differences in rates at which the individual molecules of the mixture migrate through a stationary medium under the influence of a moving phase, or in bind and elute processes.

The term "chromatography resin" or "chromatography media" are used interchangeably herein and refer to any kind of phase (e.g., a solid phase) which separates an analyte of interest (e.g., a target molecule) from other molecules present in a mixture. Usually, the analyte of interest is separated from other molecules as a result of differences in rates at which the individual molecules of the mixture migrate through a stationary solid phase under the influence of a moving phase, or in bind and elute processes. Examples of various types of chromatography media include, for example, cation exchange resins, affinity resins, anion exchange resins, anion exchange membranes, hydrophobic interaction resins and ion exchange monoliths.

The term "capture step" as used herein, generally refers to a method used for binding a target molecule with a stimulus responsive polymer or a chromatography resin, which results in a solid phase containing a precipitate of the target molecule and the polymer or resin. Typically, the target molecule is subsequently recovered using an elution step, which removes the target molecule from the solid phase, thereby resulting in the separation of the target molecule from one or more impurities. In various embodiments, the capture step can be conducted using a chromatography media, such as a resin, membrane or monolith, or a polymer, such as a stimulus responsive polymer, polyelectrolyte or polymer which binds the target molecule.

The term "salt," as used herein, refers to a compound formed by the interaction of an acid and a base. Various salts which may be used in various buffers employed in the methods described herein include, but are not limited to, acetate (e.g. sodium acetate), citrate (e.g., sodium citrate), chloride (e.g., sodium chloride), sulphate (e.g., sodium sulphate), or a potassium salt.

The term "solvent," as used herein, generally refers to a liquid substance capable of dissolving or dispersing one or more other substances to provide a solution. Solvents include aqueous and organic solvents, where useful organic solvents include a non-polar solvent, ethanol, methanol, isopropanol, acetonitrile, hexylene glycol, propylene glycol, and 2,2-thiodiglycol.

The term "parts per million" or "ppm," as used interchangeably herein, refers to a measure of purity of a desired target molecule (e.g., a target protein or antibody) purified using a stimulus responsive polymer described herein. Accordingly, this measure can be used either to gauge the amount of a target molecule present after the purification process or to gauge the amount of an undesired entity. In some embodiments, the units "ppm" are used herein to refer to the amount of an impurity in a solution, e.g., HCP or CHOP, in nanograms/milliliter of protein of interest in milligrams/milliliter (i.e., CHOP ppm=(CHOP ng/ml)/(protein of interest mg/ml). When the proteins are dried (e.g., by lyophilization), ppm refers to (CHOP ng)/(protein of interest mg)).

The term "pI" or "isoelectric point" of a polypeptide, as used interchangeably herein, refers to the pH at which the polypeptide's positive charge balances its negative charge. pI can be calculated from the net charge of the amino acid residues or sialic acid residues of attached carbohydrates of the polypeptide or can be determined by isoelectric focusing.

The terms "bind and elute mode" and "bind and elute process," as used herein, refer to a separation technique in which at least one target molecule contained in a sample (e.g., an Fc region containing protein) binds to a suitable resin or media (e.g., an affinity chromatography media or a cation exchange chromatography media) and is subsequently eluted.

The terms "flow-through process," "flow-through mode," and "flow-through operation," as used interchangeably herein, refer to a separation technique in which at least one target molecule (e.g., an Fc-region containing protein or an antibody) contained in a biopharmaceutical preparation along with one or more impurities is intended to flow through a material, which usually binds the one or more impurities, where the target molecule usually does not bind (i.e., flows through).

The term "process step" or "unit operation," as used interchangeably herein, refers to the use of one or more methods or devices to achieve a certain result in a purification process. Examples of process steps or unit operations which may be employed in the processes and systems described herein include, but are not limited to, clarification, bind and elute chromatography, virus inactivation, flow-through purification and formulation. It is understood that each of the process steps or unit operations may employ more than one step or method or device to achieve the intended result of that process step or unit operation. For example, in some embodiments, the clarification step and/or the flow-through purification step, as described herein, may employ more than one step or method or device to achieve that process step or unit operation. In some embodiments, one or more devices which are used to perform a process step or unit operation are single-use devices and can be removed and/or replaced without having to replace any other devices in the process or even having to stop a process run.

As used herein the term "pore size" and "nominal pore size" refers to the pore size which retains the majority of the particulate at 60-98% of the rated pore size.

As used herein the term "throughput" means the volume filtered through a filter.

As used herein, the term "system" generally refers to the physical form of the whole purification process, which includes two or more process steps or unit operations, as described herein. In some embodiments, the system is enclosed in a sterile environment.

In the present invention, the use of open graded layers allows the larger particles to penetrate and become captured within the depth of the filters, rather than collecting on the surface (Refer to Examples 2A and 2B).

The advantage is higher throughput, and retention of large solids (0.5 microns to about 200 microns) while eliminating the problem of cake formation. The use of open pores in the primary clarification filters provides these depth filters with the linear increase in pressure with the solid retention with no significant increase in the pressure and hence resulting in high throughputs. The structural dimension of the filter in combination with the optimization of layers (pore sizes and thickness) gives exceptional filtration properties which can retain high amount of solids.

In the present invention, the use of open graded layers allows the larger flocculated particles in the feed stream to penetrate into the depth of the filter, and become captured within the pores of the filter rather than collect on the surface (Refer to Examples 9 (A-E) and 11 (A-J)). The primary clarification depth filter provided herein are arranged such that the "open" top layers constitute the prefiltration zone of the depth filters in order to capture larger flocculated particles, while the bottom layers constitute the polishing zone which captures the smaller residual aggregated flocculated particles. One advantage with the primary clarification depth filter having this type of arrangement is higher throughput, and the retention of larger flocculated solids, while also eliminating the problem of cake formation. The use of such open pores in the primary clarification filter taught herein provides a linear increase in pressure with the solids retention, with no significant increase in the pressure, and hence resulting in higher, more desirable throughputs.

Examples of primary clarification depth filters according to the invention are depicted in FIGS. 1A, 1B, 1C, 1D, 1E and 1F.

Figure 1B:
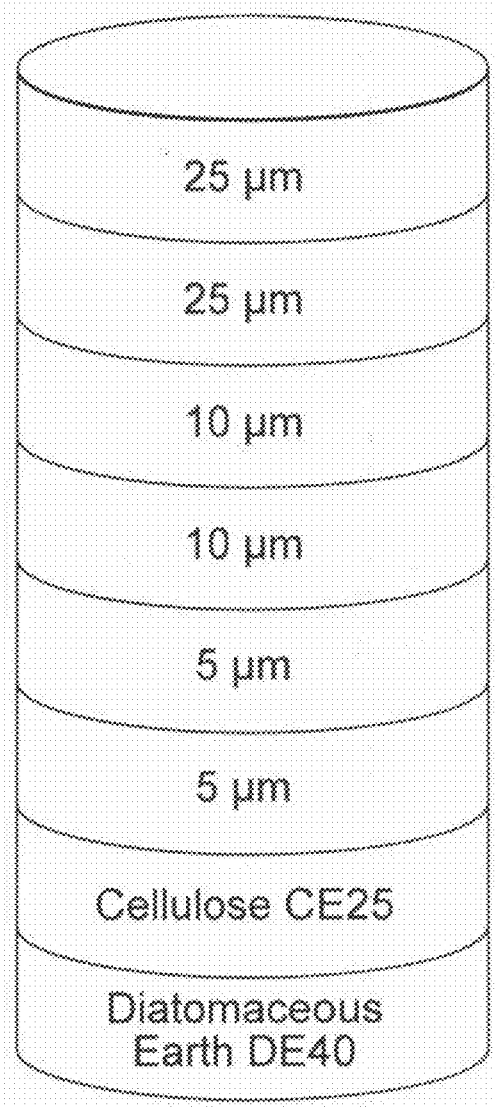
Figure 1C:
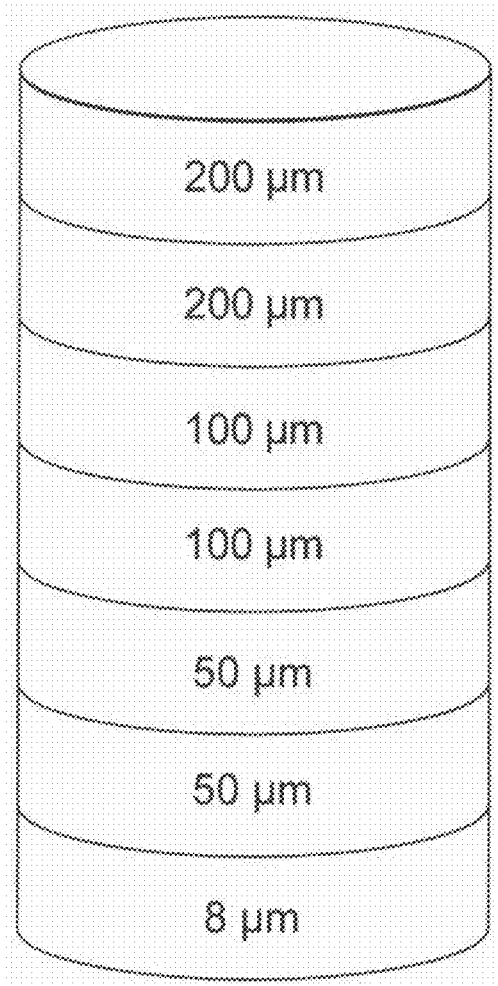

FIG. 1C depicts a primary clarification depth filters having at least seven layers, and is used when the cell-culture feeds are treated with a polymer flocculant (e.g., smart polymer or traditional flocculant).

Figure 1D:
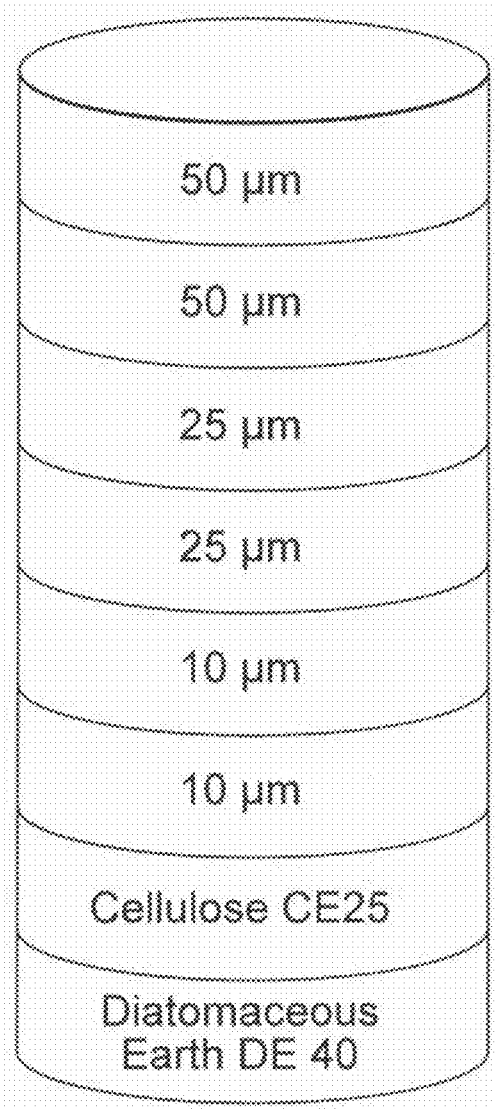
Figure 1E:
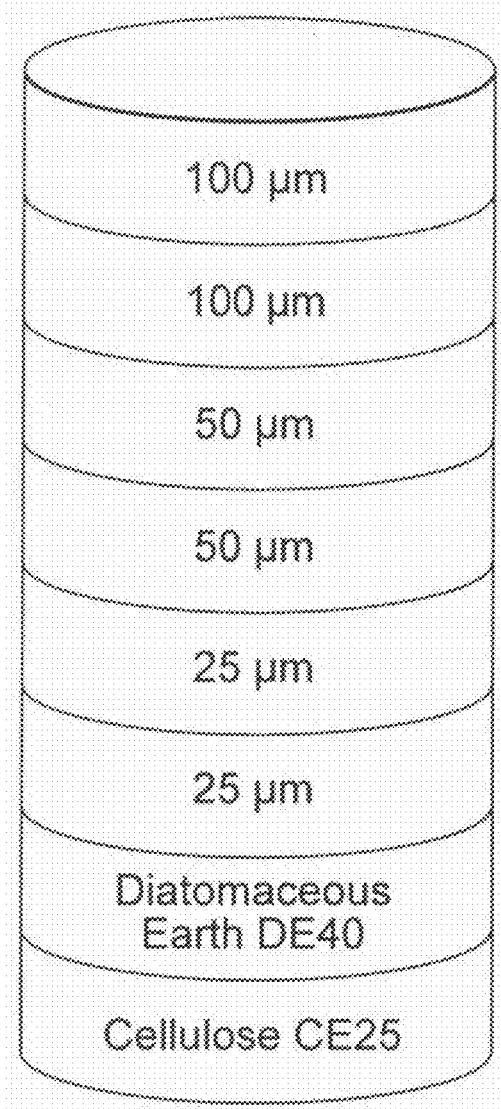

FIGS. 1A and 1E depict primary clarification depth filters having at least eight layers, and are each used when the cell-culture feeds are treated with a polymer flocculant (e.g., smart polymer or traditional flocculant).

Figure 1F:
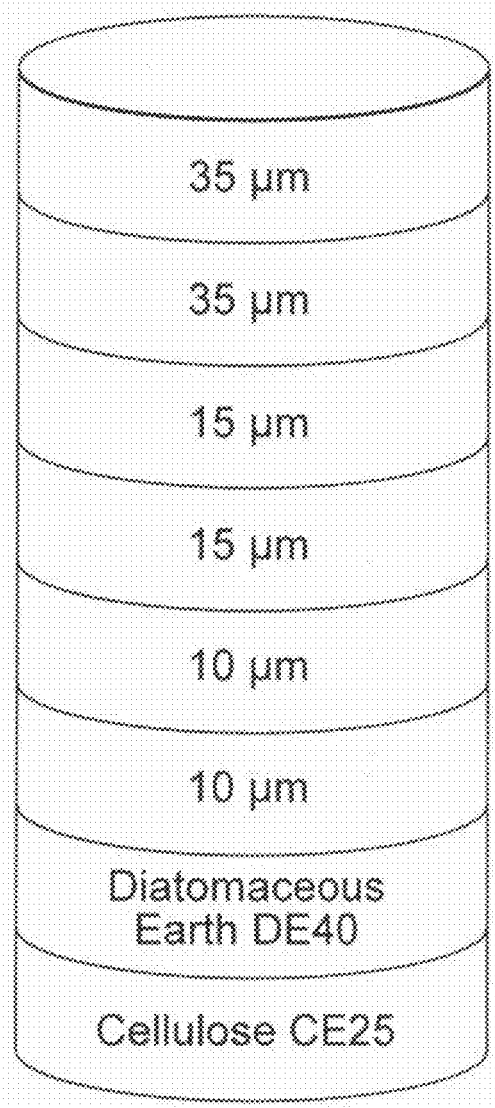
Figure 2:
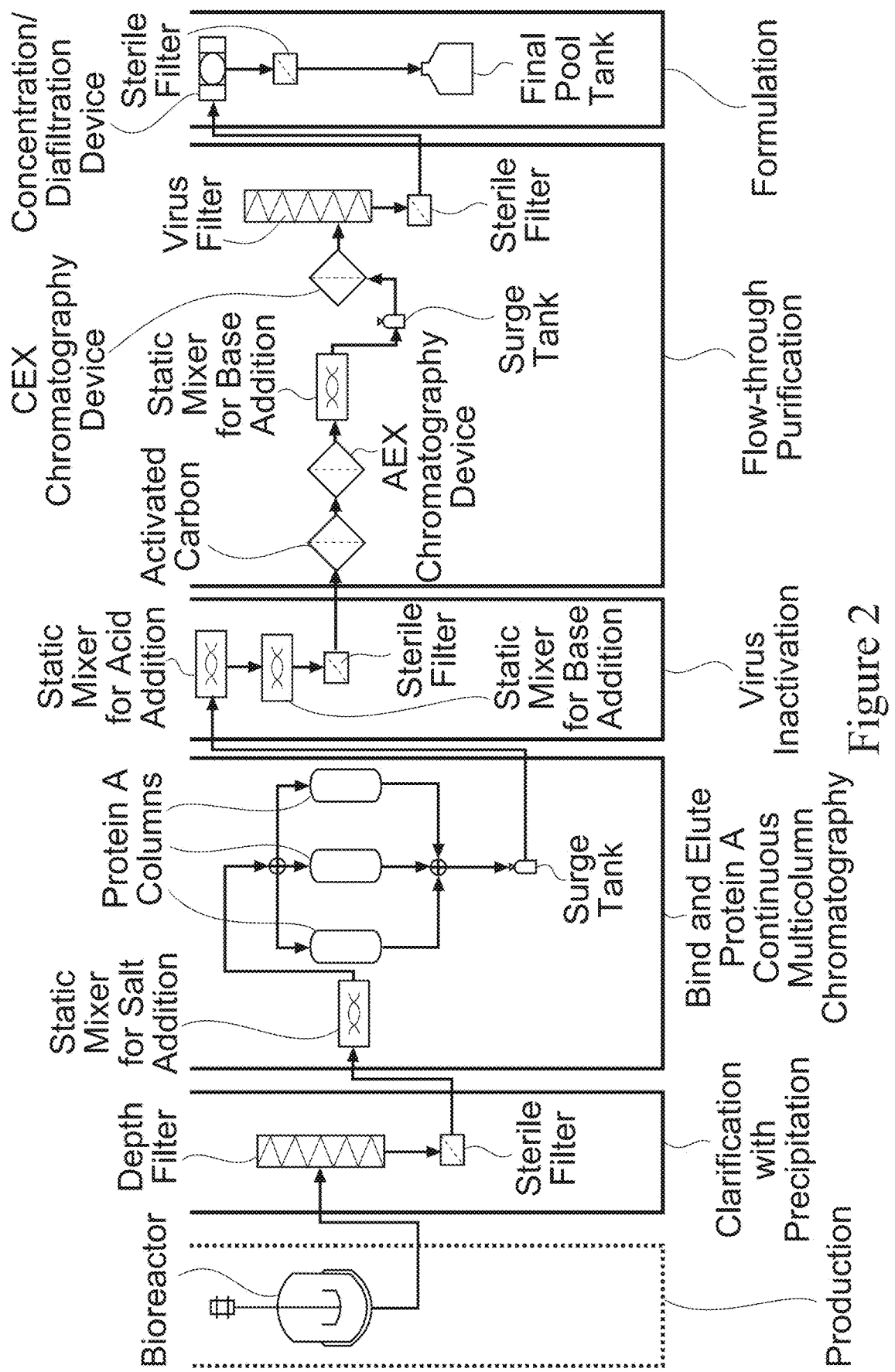
FIG. 2 is a schematic representation of an exemplary primary clarification depth filter purification process, as described herein. The purification process shown uses a bioreactor for cell culture followed by the following process steps: primary clarification depth filtration; Protein A bind and elute chromatography (capture); virus inactivation; flow-through purification; and formulation. As shown, each of the process steps employs one or more devices used to achieve the intended result of the process step. As shown, clarification employs a graded clarification depth filtration as taught herein and depicted in FIGS. 1A to 1F; Protein A bind and elute chromatography is performed using continuous multicolumn chromatography (CMC); virus inactivation employs two in-line static mixers; flow-through purification employs activated carbon (AC) followed by anion exchange (AEX) chromatography followed by a pH change using an in-line static mixer and a surge tank followed by flow-through cation exchange (CEX) chromatography and virus filtration; and formulation employs a diafiltration/concentration tangential flow filtration device followed by sterile filtration. One or more sterile filters are also employed throughout the process.
Figure 3C:
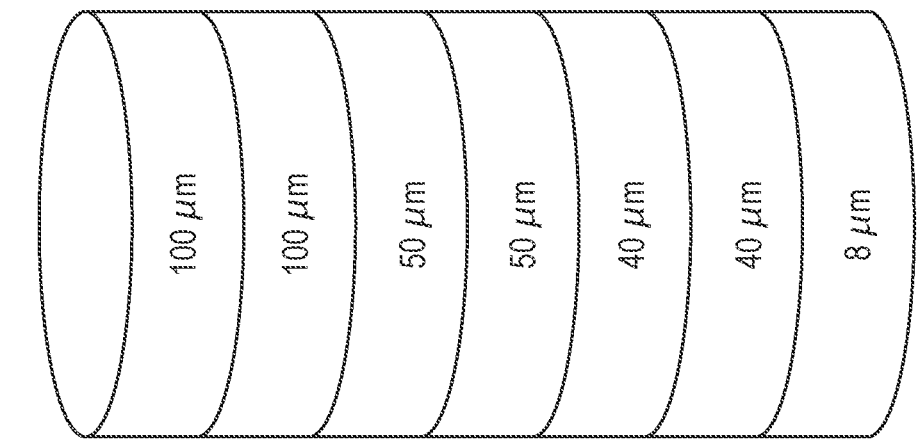
FIGS. 3A, 3B and 3C depict different schematic embodiments of examples of primary clarification depth filters according to the invention.
Figure 3B:
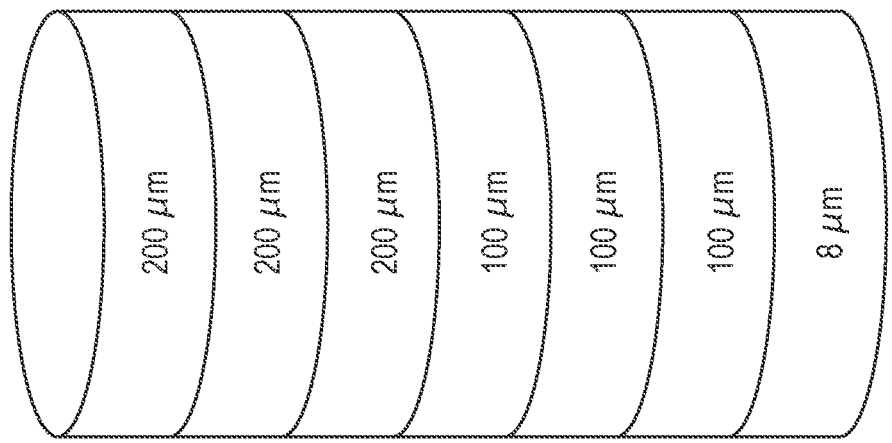
Figure 3A:
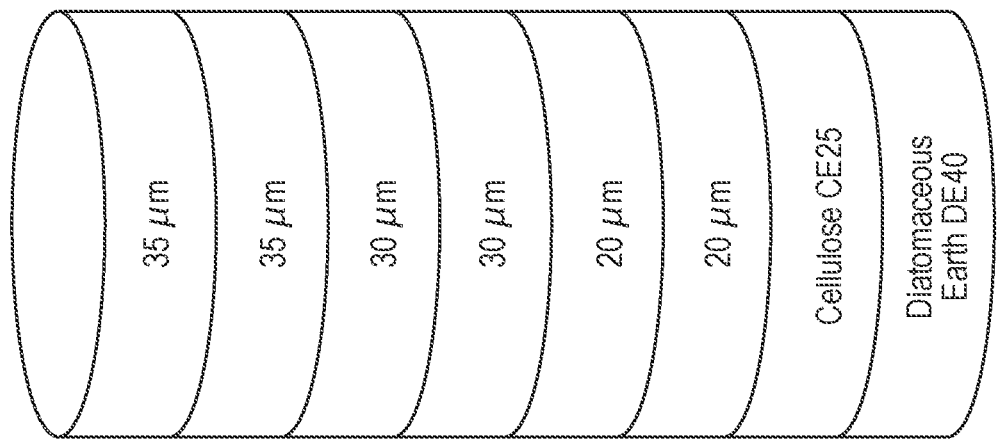

FIGS. 1B, 1D, and 1F depict primary clarification depth filters having at least eight layers, and are each used when the cell-culture feeds are chemically treated (e.g., acid treatment).

The primary clarification depth filter depicted in FIG. 1A shows a primary clarification depth filter used when the cell-culture feeds are treated with a polymer flocculant (e.g., smart polymer) having two (upper) layers with a nominal pore size of about 100 microns of a non woven such as polypropylene about 0.4 cm thick, having two more layers with a nominal pore size of about 50 microns of a non woven such as polypropylene about 0.4 cm thick, having two additional layers with a nominal pore size of about 25 microns of a non woven such as polypropylene about 0.4 cm thick, followed by a single layer about 0.35 cm thick of a material such as cellulose (CE25) for example, and another single layer about 0.35 cm thick of a material such as diatomaceous earth (DE40) for example.

The primary clarification depth filter depicted in FIG. 1B shows a primary clarification depth filter used when the cell-culture feeds are chemically treated (e.g., acid treatment) having two (upper) layers with a nominal pore size of about 25 microns of a non woven such as polypropylene about 0.4 cm thick, having two more layers with a nominal pore size of about 10 microns of a non woven such as polypropylene about 0.4 cm thick, having two additional layers with a nominal pore size of about 5 microns of a non woven such as polypropylene about 0.4 cm thick, followed by a single layer about 0.35 cm thick of a material such as cellulose (CE25) for example, and followed by another single of layer about 0.35 cm thick of a material such as diatomaceous earth (DE40) for example. Either the cellulose or diatomaceous earth layer can be selected as the lowest (bottom) layer.

The primary clarification depth filter depicted in FIG. 1C shows a primary clarification depth filter used when the cell-culture feeds are treated with a polymer flocculant (e.g., smart polymer) having two (upper) layers with a nominal pore size of about 200 microns comprising a non woven such as polypropylene about 0.4 cm thick, having two more layers with a nominal pore size of about 100 microns of a non woven such as polypropylene about 0.4 cm thick, having two additional layers with a nominal pore size of about 50 microns comprising a non woven such as polypropylene about 0.4 cm thick, followed by a single layer (bottom) about 8 microns thick of a non woven such as polypropylene about 0.2 cm thick.

The primary clarification depth filter depicted in FIG. 1D shows a primary clarification depth filter used when the cell-culture feeds are chemically treated (e.g., acid treatment) having two (upper) layers with a nominal pore size of about 50 microns comprising a non woven such as polypropylene about 0.4 cm thick, having two additional layers with a nominal pore size of about 25 microns of a non woven such as polypropylene about 0.4 cm thick, having two more layers with a nominal pore size of about 10 microns of a non woven such as polypropylene about 0.4 cm thick, followed by a single layer about 0.35 cm thick of a material such as cellulose (CE25) for example, and followed by another single of layer about 0.35 cm thick of a material such as diatomaceous earth (DE40) for example. Either the cellulose or diatomaceous earth layer can be selected as the lowest (bottom) layer.

The primary clarification depth filter depicted in FIG. 1E shows a primary clarification depth filter used when the cell-culture feeds are treated with a polymer flocculant (e.g., smart polymer) having two (upper) layers with a nominal pore size of about 100 microns comprising a non woven such as polypropylene about 0.4 cm thick, having two more layers with a nominal pore size of about 50 microns of a non woven such as polypropylene about 0.4 cm thick, having two additional layers with a nominal pore size of about 25 microns comprising a non woven such as polypropylene about 0.4 cm thick, followed by a layer about 0.35 cm thick of a material such as cellulose (CE25) for example, and followed by another single of layer about 0.35 cm thick of a material such as diatomaceous earth (DE40) for example.

The primary clarification depth filter depicted in FIG. 1F shows a primary clarification depth filter used when the cell-culture feeds are chemically treated (e.g., acid treatment) having two (upper) layers with a nominal pore size of about 35 microns comprising a non woven such as polypropylene about 0.4 cm thick, having two more layers with a nominal pore size of about 15 microns of a non woven such as polypropylene about 0.4 cm thick, having two additional layers with a nominal pore size of about 10 microns comprising a non woven such as polypropylene about 0.4 cm thick, followed by a single layer about 0.35 cm thick of a material such as cellulose (CE25) for example, and followed by another single of layer 0.35 cm thick of a material such as diatomaceous earth (DE40) for example. Either the cellulose or diatomaceous earth layer can be selected as the lowest (bottom) layer.

The structural dimension of the primary clarification depth filter provided herein in combination with the optimization of the pore sizes and/or thickness of layer of the primary clarification depth filter results in highly advantageous filtration properties which also retain high amounts of solids. Since depth filters achieve filtration through the depth of media via a combination of various mechanisms, the column volume of feed ($V_f$) versus column volume of media ($V_m$) shows the effectiveness of different filters.

In addition, various feeds have different amounts of solids which result in the highly variable performance of the depth filters, hence ($V_f$) versus ($V_m$) value gives a better estimate of the actual "efficiency" of filters.

Another important parameter, K, is used to describe the filter efficiency while normalizing for the solid content of the feedstock. The parameter K allows for filtration of feeds with different solids content to be effectively compared.

The K parameter is actually function of three measureable parameters, volume throughput (TP), collection efficiency ($\eta$), and initial concentration of solids ($C_i$) as shown in Equation 1.

$$K = [TP] \times [\eta] \times [C_i] \times 100 \quad (1)$$

Where volume throughput (TP) is given by volume of feed filtered ($V_f$) divided by volume of media ($V_m$), collection efficiency ($\eta$) is given by volume of solids captured ($V_{sc}$) divided by volume of solids in the feed (Vs), and initial concentration of solids ($C_i$) is given by volume of solids in the feed (Vs) divided by volume of feed filtered ($V_f$) as given in Equation 2.

$$K = \left[\frac{V_f}{V_m}\right] \times \left[\frac{V_{sc}}{V_s}\right] \times \left[\frac{V_s}{V_f}\right] \times 100 \quad (2)$$

The following examples will demonstrate the usefulness of Equations (1) and (2) and the K parameter in determining and comparing the efficiency of particle depth filters when used with particular feedstocks.

The following examples are provided so as to provide those of ordinary skill in the art with a complete disclosure and description of how to make the compositions of the invention and how to practice the methods of the invention and are not intended to limit the scope of what the inventor regards as his invention. Efforts have been made to insure accuracy with respect to numbers used (e.g. amounts, temperature, etc.), but some experimental errors and deviation should be accounted for. Unless indicated otherwise, temperature is in degrees C., chemical reactions were performed at atmospheric pressure or transmembrane pressure, as indicated, the term "ambient temperature" refers to approximately 25° C. and "ambient pressure" refers to atmospheric pressure.

COMPARATIVE EXAMPLES

Settling often fails because of long settling time (hours). Disposing large volume of unconsolidated cell floc mass causes low mAb yield as a significant fraction of the mAb is trapped in the cell mass. (Refer to Example 5)

Cake filtration fails because the cell mass breaks down under pressure. In other words, cell debris break apart from the polymer under stress and flow through as high turbidity in the filtrate (refer to Example 6).

Depth filtration fails because the flocs, particularly those from polymer systems, are quite large, in the order of 100 microns. Instead of penetrating into the media, which is needed for depth filtration, large flocs soon pile up on top of the surface of the depth filter media, reducing the depth filter media into an inefficient cake filter. (refer to Example 7)

Dynamic filtration such as tangential filtration or vibrated filter media have been tried with little success because the shear stress needed to reduce cake formation break up the flocs back into individual particles, nullifying the benefits of flocculation. (refer to Example 8)

The invention will be further clarified by the following examples which are intended to be exemplary of the invention.

EXAMPLES

Example 1

Preparation of Unclarified Non-Expressing Cell Culture Fluid (CCF)

In a representative experiment, cells derived from an expressing Chinese Hamster Ovary (CHO) cell line were grown in a 10 L bioreactor (New Brunswick Scientific, Edison, N.J.) to a density of $10 \times 10^6$ cells/mL and harvested at 80% viability. Monoclonal antibody (mAb) titer was determined to be 0.8 g/L. The level of host cell proteins (HCP) was found to be 200,000 ng/mL using an ELISA assay (Cygnus Technologies, Southport, NC, #3G ELISA). The pH of the unclarified cell culture was pH 6.9.

Example 2

Preparation of Multivalent Ion Stimulus Sensitive Polymer.

10 g of polyallylamine (PAA) (Nittobo Medical Co., Ltd., Tokyo, Japan 150 kD; 40% wt/wt) is placed in a 100 mL round bottom flask and a solution of 3.34 g of sodium hydroxide (1.2 Eq. per monomer) in 25 mL $H_2O$ is added at room temperature under magnetic stirring and in small amounts. Benzyl chloride (2.30 g, 2.09 mL) is then added, stirred for few minutes at room temperature and then heated to 60° C. overnight for 17 hours. The reaction is then cooled to room temperature and solvent is removed resulting in polymer precipitation. The precipitated polymer is washed with water and stirred in 1M aqueous AcOH solution (40 ml) until complete solubilization is achieved. The solution is then diluted with $H_2O$ to a final volume of 400 ml (1% polymer solution), potassium dibasic phosphate ($K_2HPO_4$) (3.48 g) is added under stirring and pH of the solution is adjusted to pH 6.8 to precipitate the modified polymer. The polymer is collected by filtration over a fritted funnel and finally dried overnight in a vacuum oven overnight at 50° C. to 60° C. The polymer was then redissolved in 1M acetic acid to generate a 10% wt polymer concentrate solution.

Example 3

Smart Polymer (SmP) Treatment of CHO-S Feed.

In order to flocculate the cell culture with SmP, a 500 ml sample of cell culture broth from Example 1 was added to a 1000 ml media bottle. While stirring, a sample of polymer concentrate from Example 2 to the desired polymer dose (wt %), typically 0.2%. The solution was allowed to mix for 15 minutes.

Example 4

Acid Treatment of CHO-S Feed.

In order to flocculate the cell culture with addition of acid to reduce pH, a 500 ml sample of cell culture broth from Example 1 was added to a 1000 ml media bottle. While stirring, concentrated acetic acid was added dropwise until the desired pH was achieved. The target pH was pH 4.8-5.0 unless otherwise noted. The solution was allowed to mix for 15 minutes.

Example 5

Settling Studies for the Smart Polymer (SmP) Treated CHO-S Feed.

Settling experiments were conducted at different settling times to determine effectiveness of using density differences to perform the solid liquid separation of SmP treated feeds. 500 ml of cell culture broth was prepared according to Example 3.

The SmP treated feed was allowed to settle for about 0.5 to 6 hours, and samples of the supernatant were taken and measured for turbidity and volume of solids. The turbidity was measured using a HACH Model #2100P turbiditimeter. Table 1 shows the settling studies on SmP treated CHO-S feed for times varying from 0.5 to 6 hours.

It was observed that the settling time was >about 180 minutes to reach the equilibrium turbidity of <about 20 NTU for the SmP treated CHO-S feed, and about 120 minutes to reach the equilibrium turbidity of <about 20 NTU for the SmP treated CHO-DH44 feed.

When the smallest polymer dose (0.05%) was used, the incomplete flocculation lead to increased turbidity (>about 350 NTU) even after 12 hours settling time for the SmP treated CHO-S feed. In addition, the settling times of 3 hours has a large volume of unconsolidated cell mass (about 30% to 40%) for SmP treated CHO-S feed and 20% for the SmP treated CHO-DH44 feed which could apparently resulted in low mAb yield (about 60% to 80%) as significant amount of mAb is trapped in the unconsolidated mass.

TABLE 1

Settling studies for the smart polymer treated CHO-S feed.

| Time (min) | Turbidity (0.05%) (NTU) | Turbidity (0.2%)(NTU) | Turbidity (0.4%)(NTU) | Turbidity (0.6%)(NTU) |
|---|---|---|---|---|
| 0 | 451 | 549 | 601 | 666 |
| 60 | 128 | 26 | 81 | 112 |
| 120 | 101 | 16 | 54 | 90 |
| 180 | 98 | 10 | 38 | 68 |

Example 6

Cake Filtration for the Smart Polymer (SmP) Treated DG44 and CHO-S Feeds

Diamatoceous earth (DE) media was used to determine the effectiveness of the cake filtration. First, DE was packed to a depth of least about 4 cm in the Buchner funnel after which we passed the SmP treated feed from Example 3 by applying vacuum through it. During filtration through the diatomaceous earth media, CHO-S cells formed a film of filter cake on the 20 µm sieve. It was observed that the filter cake impeded the outward flow of filtrate resulting in a throughput<about 10 L/m². In addition, it was observed that the cell mass broke apart from the polymer under stress resulting in a high turbid filtrate (about 200 NTU to 300 NTU) which can significantly impact the secondary filtration operations.

Example 7

Depth Filtration for the Smart Polymer (SmP) Treated CHO-S Feeds Using commercially available primary clarification filters (D0HC and F0HC).

Filtration experiments were performed with smart polymer (SmP) treated CHO-S feed from Example 3 and acid treated feed from Example 4 to determine the throughput of commercially available MilliStak® D0HC depth filters. The D0HC filters were flushed with water according to the user instructions. Feed was applied to the depth filters using a peristaltic pump at a flow rate of about 100 L/m$^2$/hr. However, depth filters were unable to handle high-solids feed-streams. It is believed that depth filtration primarily failed because the aggregated cells were larger and instead of penetrating into the media, which is needed for depth filtration, larger particulates build up on the top of the depth filter media surface, reducing the depth filter media into an inefficient cake filter. D0HC had a throughput of about 20 L/m$^2$ for the SmP treated feeds and F0HC had a throughput of about 5 L/m$^2$ for the acid treated feeds. The filter cake formation from the larger floc particles is largely due to the tightness of filter which reduced the throughput of filters significantly.

Example 8

Dynamic Filtration for the Smart Polymer (SmP) Treated Feed.

Dynamic filtration experiments using tangential flow Pellicon® 3 (0.11 m$^2$) filtration devices (available from Millipore Corporation, Billerica, Mass. USA) was performed to determine the effectiveness of solid liquid separation of SmP treated feed. The filtration devices contained microfiltration membranes (0.45 μm) constructed of a polyvinyldifluoride (PVDF) membrane. SmP treated cell culture harvest was loaded at 50 L/m$^2$/h until the TMP reached 15 psi. An instantaneous plugging of the Pellicon® 3 devices was observed, resulting in a throughput<5 L/m$^2$. Poor yield was observed due to the material loss created by the rapid plugging and system and device hold-up volume.

Example 9A

Depth filters for the removal of aggregated and large biomolecule particulates.

A depth filtration device 10 was assembled using seven (7) layers of non-woven fibers (polypropylene) having a total thickness of all the layers of 1.6 cm. The layers are arranged in the depth filtration device from most open nominal pore size 200 μm (2 layers) followed by nominal 50 μm (2 layers), nominal 40 μm (2 layers) to a single nominal 8 μm layer (see FIG. 1).

The individual properties of the seven (7) layers of (needle felt) non-woven fibers (Rosedale Products, Inc., Ann Arbor, Mich.) are shown in Table 3 (2 layers×200 μm, 2 layers×50 μm, 2 layers×40 μm, and 1 layers×8 μm). After assembling the stack of layers, polypropylene hose barb end caps were added to the top and bottom and the entire assembly overmolded into a single, integral Mini Cap filtration device (available from Millipore Corporation, Billerica, Mass. USA). The depth filtration device was tested for water permeability resulting in a value of 0.45 L/min at 4 psi.

TABLE 3

Characterization of physical properties of non-woven felt material from Rosedale Products, Inc. and Midwest Filtration Company

| Supplier | Layer | Nom. Pore (μm) | Av. Pore (μm) | Basis Weight (g/m$^2$) | Water Flow Rate (gallons/min) |
|---|---|---|---|---|---|
| Rosedale | Needle Punch | 200 | 100 | 425 | 555 |
| Rosedale | Needle Punch | 100 | 85 | 380 | 529 |
| Rosedale | Needle Punch | 50 | 70 | 309 | 524 |
| Rosedale | Needle Punch | 40 | 70 | 347 | 514 |
| Rosedale | Needle Punch | 30 | 60 | 320 | 523 |
| Rosedale | Needle Punch | 25 | 50 | 266 | 492 |
| Rosedale | Needle Punch | 20 | 40 | 413 | 330 |
| Rosedale | Needle Punch | 10 | 35 | 396 | 360 |
| Rosedale | Melt Blown | 8 | 8 | 288 | 264 |
| Midwest | UniPro 760 PP (Needle Punch) | ≥200 | 110 | 260 | 552 |
| Midwest | Needle Punch | 200 | 80 | 336 | 500 |
| Midwest | Needle Punch | 100 | 70 | 369 | 497 |
| Midwest | Needle Punch | 50 | 65 | 335 | 476 |
| Midwest | Needle Punch | 25 | 50 | 390 | 436 |
| Midwest | Needle Punch | 10 | 35 | 390 | 410 |
| Midwest | Needle Punch | 5 | 31 | 368 | 400 |
| Midwest | Needle Punch | 1 | 30 | 486 | 350 |
| Midwest | UniPro 530 MM (Melt Blown) | ≤1 | 15 | 187 | 338 |

Example 9B

Depth Filters for the Removal of Aggregated and Large Biomolecule Particulates.

The graded depth filter of Example 9B consists of graded non-woven fibers, having a depth of 1.6 cm, and are capable of filtering an acid flocculated feed stream comprising particles in the range of about 0.5 μm to about 200 μm. The graded depth filter consists of seven (7) layers of non-woven fibers from Rosedale Products, Inc., Ann Arbor, Mich. (2 layers×200 μm, 2 layers×100 μm, 2 layers×50 μm, and 1 layer×8 μm). After assembling the stack of layers, polypropylene hose barb end caps were added to the top and bottom and the entire assembly overmolded into a single, integral Mini Cap filtration device (available from Millipore Corporation, Billerica, Mass. USA). The device was tested for water permeability resulting in a value of 0.55 L/min at 4 psi.

Example 9C

Depth Filters for the Removal of Aggregated and Large Biomolecule Particulates.

The graded depth filter of Example 9C consists of graded non-woven fibers, have a depth of 1.6 cm, and are capable of filtering an acid flocculated feed stream comprising particles in the range of about 0.5 μm to about 200 μm. The graded depth filter consists of seven (7) layers of non-woven fibers from Rosedale Products, Inc., Ann Arbor, Mich. (3 layers×200 μm, 3 layers×100 μm and 1 layer×8 μm). The graded depth filter provided herein was assembled in a 23 cm$^2$ of an integral Mini Cap filtration device (available from Millipore Corporation, Billerica, Mass. USA) and tested for water permeability resulting in a value of 0.55 L/min at 4 psi.

Example 9D

Depth Filters for the Removal of Aggregated and Large Biomolecule Particulates.

The graded depth filter of Example 9D consists of graded non-woven fibers, have a depth of 1.6 cm, and are capable of filtering an acid flocculated feed stream comprising particles in the range of 0.5 μm to 100 μm. The graded depth filter consists of seven (7) layers of non-woven fibers from Rosedale Products, Inc., Ann Arbor, Mich. (2 layers×100 μm, 2 layers×50 μm, 2 layers×40 μm and 1 layer×8 μm). After assembling the stack of layers, polypropylene hose barb end caps were added to the top and bottom and the entire assembly overmolded into a single, integral Mini Cap filtration device (available from Millipore Corporation, Billerica, Mass. USA) filtration device. The device was tested for water permeability resulting in a value of 0.5 L/min at 4 psi.

Example 9E

Depth Filters for the Removal of Aggregated and Large Biomolecule Particulates.

The graded depth filter of Example 9E consists of a graded non-woven fibers, have a depth of 1.6 cm, and are capable of filtering a polymer flocculated feed stream comprising particles in the range of about 0.5 μm to about 200 μm. The graded depth filter consists of seven (7) layers of non-woven fibers from Midwest Filtration Company, Cincinnati, Ohio (2 layers×UniPro® 760 PP, 2 layers×100 μm, 2 layers×50 μm and 1 layer×UniPro® 530 MM). The graded depth filter feeds consists of seven (7) layers of non-woven fibers from Midwest Filtration Company, Cincinnati, Ohio (2 layers×UniPro® 760 PP, 2 layers×100 μm, 2 layers×50 μm and 1 layer×UniPro® 530 MM). The graded depth filter provided herein was assembled in a 23 cm² integral Mini Cap filtration device (available from Millipore Corporation, Billerica, Mass. USA) and tested for water permeability resulting in a value of 0.65 L/min at 4 psi.

Example 10

Filtration Performance of Depth Filters Removal of Aggregated and Large Biomolecule Particulates Filter devices from Examples 9A-9E were tested for filtration performance using the following method. The depth filters were run with untreated and SmP treated unclarified feed after flushing out with the Milli-Q water with the TMP across each filter monitored by pressure transducers. The unclarified cell culture harvest was treated with 0.2 wt % smart polymer (SmP) dose (wt %) and stirred for 15 minutes. The depth filters were first flushed with about 50 L of Milli-Q water for each square meter of filter area at 600 L/m²/h to wet the filter media and flush out extractables. Untreated and SmP treated unclarified harvest were loaded at 100 L/m²/h until the TMP across an y one filter reached 20 psig.

Table 4 compares the filter throughput of two Millistak® filters (X0HC and D0HC) with Primary clarification depth filter for the filtration of the feed described in Example 3. (0.2% (w/v) smart polymer (SmP) treated feed). X0HC and D0HC gave a throughput of 10 L/m² and 44 L/m² whereas throughput of primary clarification depth filter was 325 L/m². Filtrate turbidity in all the cases was <about 5 NTU as shown in Table 4. In terms of column volume of filtrate by column volume of media, X0HC and D0HC gave a throughput of 1.5 $V_f/V_m$ and 6 $V_f/V_m$ whereas throughput of primary clarification depth filter was 16.5 $CV_f/CV_m$. Example 9A performed the best with the volume throughput of 16.5 $V_f/V_m$ (325 L/m²) with a K efficiency of 84%. From this comparison, it is evident that Example 9A filter composed of layers described in the present claim is capable of removing large amount of solids during clarification of unclarified cell harvests.

TABLE 4

Comparison of the Primary Clarification (PC) Depth Filter described in Example 9A for the filtration throughput of SMP treated feed with 0.2% (w/v).

| Feed | Treatment | Filter Type | Dose (%) (w/v) | PCV (%) | Turbidity (NTU) | TP (L/m²) | TP ($V_f/V_m$) | K (%) |
|---|---|---|---|---|---|---|---|---|
| CHO-S | Untreated | X0HC | NA | 3.8 | 5 | 10 | 2 | 8 |
| CHO-S | Untreated | D0HC | NA | 3.8 | 45 | 44 | 6.5 | 26 |
| CHO-S | SMP treated | X0HC | 0.2 | 4.0 | 2 | 8 | 1.5 | 8 |
| CHO-S | SMP treated | D0HC | 0.2 | 4.0 | 2 | 39 | 6 | 24 |
| CHO-S | SMP treated | PC (Ex. 9A) | 0.2 | 4.0 | 6 | 325 | 16.5 | 66 |

The present invention has a significant advantage in terms of linear differential pressure growth. In the case of X0HC and D0HC the fluid pressure was lesser and constant at the start but suddenly increased exponentially thereby reaching its limit. One possible explanation consistent with the observed pressure response is the rapid formation of a cake layer on the surface of the filter. In the case of primary clarification depth filters, the pressure increase is close to linear, with no significant abrupt increase in pressure. This result is consistent with particulates being trapped throughout the depth of the filter avoiding the cake formation. A large increase in filter volumetric throughput is also observed, which again is consistent of depth filtration instead of the cake filtration observed in the commercial X0HC and D0HC filters.

Table 5 compares the filter throughput of primary clarification depth filters described in Examples 9B-9E in terms of column volume of feed versus column volume of media.

The graded depth filter described in the Example 9B gave the volume throughput of 32 $V_f/V_m$ (640 L/m²) with a K efficiency of 90% for SmP treated CHO-DG44 feed and volume throughput of 22 $V_f/V_m$ (430 L/m²) with a K efficiency of 90% for SmP treated CHO-S feed.

In another Example 9C, the graded depth filter resulted in the volume throughput of 33 $V_f/V_m$ (660 L/m²) with a Kman efficiency of 94% for SmP treated CHO-DG44 feed and volume throughput of 22 $V_f/V_m$ (435 L/m²) with a K efficiency of 90% for SmP treated CHO-S feed.

The graded depth filter described in the Example 9D resulted in a volume throughput of 29 $V_f/V_m$ (580 L/m$^2$) with a K efficiency of 81% for SmP treated CHO-DG44 feed and volume throughput of 20 $V_f/V_m$ (390 L/m$^2$) with a K efficiency of 81% for SmP treated CHO-S feed.

In yet another Example 9E, the graded depth filter described in the present claim resulted in a volume throughput of 33 $V_f/V_m$ (650 L/m$^2$) with a K efficiency of 92% for SmP treated CHO-S feed.

From this comparison, it is evident that Example 9A-9E, filter composed of layers described in the claims is capable of removing large amount of solids during clarification of unclarified cell harvests.

TABLE 5

Comparison of the Primary Clarification (PC) Depth Filter described in Example 9B-9E for the filtration throughput of SMP treated feed with 0.2% (w/v).

| Feed | Treatment | Filter Type | Dose (%) (w/v) | PCV (%) | Turbidity (NTU) | TP (L/m$^2$) | TP ($V_f/V_m$) | K (%) |
|---|---|---|---|---|---|---|---|---|
| CHO-DG44 | SMP treated | PC (Ex. 9B) | 0.2 | 2.8 | <5 | 640 | 30 | 90 |
| CHO-S | SMP treated | PC (Ex. 9B) | 0.2 | 4.0 | <5 | 430 | 22 | 90 |
| CHO-DG44 | SMP treated | PC (Ex. 9C) | 0.2 | 2.9 | <5 | 660 | 33 | 94 |
| CHO-S | SMP treated | PC (Ex. 9C) | 0.2 | 4.0 | <5 | 435 | 22 | 90 |
| CHO-DG44 | SMP treated | PC (Ex. 9D) | 0.2 | 2.9 | <5 | 580 | 29 | 81 |
| CHO-S | SMP treated | PC (Ex. 9D) | 0.2 | 4.0 | <10 | 390 | 20 | 80 |
| CHO-S | SMP treated | PC (Ex. 9E) | 0.2 | 3.0 | <5 | 650 | 33 | 92 |

Example 11A

Depth Filters for the Removal of Aggregated and Small Biomolecule Particulates.

Chemically treated feeds (e.g., acid treatment) has the capability to increase the average particle size from <about 5 μm to >about 20 μm. In addition, the acid treated feeds gives a broad particle size distribution. In response to the need for separation of this broad range of particles, a combination of open graded non-woven layers and tighter (CE and DE) provides the effective depth filtration. A depth filtration device was assembled using eight (8) layers of non-woven fibers (polypropylene) having a total thickness of all the layers of 2.0 cm. The layers are arranged in the filtration device 50, FIG. 1, with the open nominal pore size 200 μm (2 layers), followed by nominal 50 μm (2 layers), nominal 40 μm (2 layers), followed by a layer of Cellulose (CE25), and a layer of diatomaceous earth (DE40). The individual properties of the six (6) layers of (needle punched) non-woven fibers (Rosedale Products, Inc., Ann Arbor, Mich.) are shown in Table 3 (2×200 μm, 2×50 μm, and 2×40 μm). After assembling the stack of layers, polypropylene hose barb end caps were added to the top and bottom and the entire assembly overmolded into a single, integral Mini Cap filtration device (available from Millipore Corporation, Billerica, Mass. USA). The device was tested for water permeability resulting in a value of 0.40 L/min at 4 psi.

Example 11B

Depth Filters for the Removal of Aggregated and Small Biomolecule Particulates.

The graded depth filter of Example 11B consists of graded non-woven fibers, have a depth of 2 cm, and are capable of filtering an acid flocculated feed stream comprising particles in the range of about 0.5 μm to about 100 μm. The graded depth filter consists of six (6) layers of non-woven fibers (2 layers×30 μm, 2 layers×25 μm, 2 layers×20 μm) from Rosedale Products, Inc., Ann Arbor, Mich., followed by a layer of cellulose (CE25), and a layer of diatomaceous earth (DE40). After assembling the stack of layers, polypropylene hose barb end caps were added to the top and bottom and the entire assembly overmolded into a single, integral Mini Cap filtration device (available from Millipore Corporation, Billerica, Mass. USA). The filtration device was tested for water permeability resulting in a value of 0.15 L/min at 4 psi.

Example 11C

Depth Filters for the Removal of Aggregated and Small Biomolecule Particulates.

The graded depth filter of Example 11B consists of graded non-woven fibers, has a depth of 2 cm, and is capable of filtering an acid flocculated feed stream comprising particles in the range of about 0.5 μm to about 100 μm. The graded depth filter feeds comprises of six (6) layers of non-woven fibers (2 layers×25 μm, 2 layers×20 μm, 2 layers×10 μm) from Rosedale Products, Inc., Ann Arbor, Mich., followed by a layer of cellulose (CE25), and a layer of diatomaceous earth (DE40). After assembling the stack of layers, polypropylene hose barb end caps were added to the top and bottom and the entire assembly overmolded into a single, integral Mini Cap filtration device (available from Millipore Corporation, Billerica, Mass. USA). The device was tested for water permeability resulting in a value of 0.15 L/min at 4 psi.

Example 11D

Depth Filters for the Removal of Aggregated and Small Biomolecule Particulates.

The graded depth filter of Example 11D consists of graded non-woven fibers, have a depth of 1.6 cm, and are capable of filtering an acid flocculated feed stream comprising particles in the range of about 0.5 μm to about 100 μm. The graded depth filter feeds comprises of four (4) layers of non-woven fibers (2×20 µm, 2×10 µm) from Rosedale Products, Inc., Ann Arbor, Mich. and cellulose (CE 25)/diatomaceous earth (DE 60). After assembling the stack of layers, polypropylene hose barb end caps were added to the top and bottom and the entire assembly overmolded into a single, integral Mini Cap filtration device (available from Millipore Corporation, Billerica, Mass. USA). The device was tested for water permeability resulting in a value of 0.3 L/min at 4 psi.

Example 11E

Depth Filters for the Removal of Aggregated and Small Biomolecule Particulates.

The graded depth filter of Example 11E consists of graded non-woven fibers, have a depth of 2 cm, and are capable of filtering an acid flocculated feed stream comprising particles in the range of about 0.5 µm to about 100 µm. The graded depth filter consists of six (6) layers of non-woven fibers from Rosedale Products, Inc., Ann Arbor, Mich. (2 layers× 25 µm, 2 layers×20 µm, 2 layers×10 µm), followed by a layer of cellulose (CE25), and a layer of diatomaceous earth (DE40). After assembling the stack of layers, polypropylene hose barb end caps were added to the top and bottom and the entire assembly overmolded into a single, integral Mini Cap filtration device (available from Millipore Corporation, Billerica, Mass. USA). The device was tested for water permeability resulting in a value of 0.2 L/min at 4 psi.

Example 11F

Depth Filters for the Removal of Aggregated and Small Biomolecule Particulates.

The graded depth filter of Example 11F consists of graded non-woven fibers, have a depth of 1.6 cm, and are capable of filtering an acid flocculated feed stream comprising particles in the range of about 0.5 µm to about 100 µm. The graded depth filter consists of four (4) layers of non-woven fibers from Rosedale Products, Inc., Ann Arbor, Mich. (2 layers×20 µm, 2 layers×10 µm), followed by a layer of cellulose (CE25), and a layer of diatomaceous earth (DE40). After assembling the stack of layers, polypropylene hose barb end caps were added to the top and bottom and the entire assembly overmolded into a single, integral Mini Cap filtration device (available from Millipore Corporation, Billerica, Mass. USA). The device was tested for water permeability resulting in a value of 0.3 L/min at 4 psi.

Example 11G

Depth Filters for the Removal of Aggregated and Small Biomolecule Particulates.

The graded depth filter of Example 11G consists of graded non-woven fibers, have a depth of 1.6 cm, and are capable of filtering an acid flocculated feed stream comprising particles in the range of about 0.5 µm to about 100 µm. The graded depth filter consists of six (6) layers of non-woven fibers from Midwest Filtration Company, Cincinnati, Ohio (2 layers×50 µm, 2 layers×25 µm, 2 layers×10 µm) followed by a layer of cellulose (CE25), and a layer of diatomaceous earth (DE40). After assembling the stack of layers, polypropylene hose barb end caps were added to the top and bottom and the entire assembly overmolded into a single, integral Mini Cap filtration device (available from Millipore Corporation, Billerica, Mass. USA). The device was tested for water permeability resulting in a value of 0.35 L/min at 4 psi.

Example 11H

Depth Filters for the Removal of Aggregated and Small Biomolecule Particulates.

The graded depth filter of Example 11H consists of graded non-woven fibers, have a depth of 2 cm, and are capable of filtering an acid flocculated feed stream comprising particles in the range of about 0.5 µm to about 100 µm. The graded depth filter consists of six (6) layers of non-woven fibers from Midwest Filtration Company, Cincinnati, Ohio (2×25 µm, 2×10 µm, 2×5 µm) followed by a layer of cellulose (CE25), and a layer of diatomaceous earth (DE40). After assembling the stack of layers, polypropylene hose barb end caps were added to the top and bottom and the entire assembly overmolded into a single, integral Mini Cap filtration device (available from Millipore Corporation, Billerica, Mass. USA). The device was tested for water permeability resulting in a value of 0.4 L/min at 4 psi.

Example 11I

Depth Filters for the Removal of Aggregated and Small Biomolecule Particulates.

The graded depth filter of Example 11I consists of graded non-woven fibers, have a depth of 2 cm, and are capable of filtering an acid flocculated feed streams comprising particles in the range of about 0.5 µm to about 100 µm. The graded depth filter comprises six (6) layers of non-woven fibers from Midwest Filtration Company, Cincinnati, Ohio (2×10 µm, 2×5 µm, 2×1 µm), followed by a layer of cellulose (CE25), and a layer of diatomaceous earth (DE40). After assembling the stack of layers, polypropylene hose barb end caps were added to the top and bottom and the entire assembly overmolded into a single, integral Mini Cap filtration device (available from Millipore Corporation, Billerica, Mass. USA). The device was tested for water permeability resulting in a value of 0.4 L/min at 4 psi.

Example 12

Filtration Performance of Depth Filters Removal of Aggregated and Small Biomolecule Particulates.

Filter devices from Examples 11A-11I were tested for filtration performance using the following method. The unclarified cell culture harvest was treated with 1M glacial acetic acid to adjust the pH to 4.8 and stirred for 30 minutes. Depth filters were run with untreated and acid treated unclarified feed after flushing out with the Milli-Q water with the TMP across each filter monitored by pressure transducers. The depth filters were first flushed with about ≥50 L of Milli-Q water for each square meter of filter area at 600 L/m²/h to wet the filter media and flush out extractables. Untreated and acid precipitated unclarified harvest were loaded at 100 L/m²/h until the TMP across any one filter reached 20 psig.

Table 6 compares the filter throughput of two Millistak® filters (X0HC and D0HC) with primary clarification depth filter for the acid treated feed. X0HC and D0HC gave a throughput of 5 L/m² and 20 L/m² whereas throughput of primary clarification depth filter was 210 L/m².

TABLE 6

Comparison of the Acid Precipitation Primary Clarification (APPC) Depth Filter for the filtration throughput for acid treated feed (pH = 4.8).

| Feed | Treatment | Filter Type | pH | PCV (%) | Turbidity (NTU) | TP (L/m$^2$) | TP (V$_f$/V$_m$) | K (%) |
|---|---|---|---|---|---|---|---|---|
| CHO-S | Untreated | X0HC | 6.9 | 3.8 | 5 | 10 | 2 | 8 |
| CHO-S | Untreated | D0HC | 6.9 | 3.8 | 45 | 44 | 6.5 | 26 |
| CHO-S | Acid treated | X0HC | 4.8 | 3.9 | 1 | 5 | 1.5 | 6 |
| CHO-S | Acid treated | D0HC | 4.8 | 3.9 | 3 | 20 | 4 | 16 |
| CHO-S | Acid treated | APPC (Ex. 11A) | 4.8 | 3.9 | 25 | 210 | 9 | 36 |

Table 2 compares the filter throughput of two Millistak® filters (X0HC and D0HC) with acid precipitated primary clarification depth filter for the acid treated feed in terms of column volume of feed versus column volume of media. X0HC and D0HC gave a throughput of 1.5 V$_f$/V$_m$ (K=6) and 4 V$_f$/V$_m$ ((K=16) whereas throughput of primary clarification depth filter was 9 V$_f$/CV$_m$(K=36). From this comparison, it is evident that Example 9A filter composed of layers described in the present claim is capable of removing large amount of solids during clarification of unclarified cell harvests.

TABLE 2

Settling studies for the smart polymer treated CHO-DG44 feed.

| Time (min) | Turbidity (0.05%) (NTU) | Turbidity (0.2%) (NTU) | Turbidity (0.4%) (NTU) | Turbidity (0.6%) (NTU) |
|---|---|---|---|---|
| 0 | >1000 | >1000 | >1000 | >1000 |
| 60 | 365 | 33 | 50 | 84 |
| 120 | 344 | 26 | 31 | 68 |
| 360 | 325 | 17 | 21 | 49 |

Table 7 compares the filter throughput of primary clarification depth filters described in Examples 11B-11I in terms of column volume of feed versus column volume of media. From this comparison, it is evident that in Examples 11A-11I, filters composed of layers as provided herein are capable of removing large amount of solids during clarification of unclarified cell harvests.

TABLE 7

Comparison of the Acid Precipitation Primary Clarification (APPC) Depth Filter for the filtration throughput for acid treated feed (pH = 4.8).

| Feed | Treatment | Filter Type | pH | PCV (%) | Turbidity (NTU) | TP (L/m$^2$) | TP (V$_f$/V$_m$) | K (%) |
|---|---|---|---|---|---|---|---|---|
| CHO-DG44 | Acid treated | APPC (Ex. 11B) | 4.8 | 2.8 | <10 | 554 | 27 | 77 |
| CHO-S | Acid treated | APPC (Ex. 11B) | 4.8 | 4.0 | <10 | 347 | 18 | 72 |
| CHO-DG44 | Acid treated | APPC (Ex. 11C) | 4.8 | 2.8 | <10 | 660 | 30 | 84 |
| CHO-S | Acid treated | APPC (Ex. 11C) | 4.8 | 4.0 | <10 | 391 | 20 | 80 |
| CHO-DG44 | Acid treated | APPC (Ex. 11D) | 4.8 | 2.8 | <10 | 580 | 29 | 81 |
| CHO-S | Acid treated | APPC (Ex. 11E) | 4.8 | 4.0 | <10 | 425 | 22 | 87 |
| CHO-S | Acid treated | APPC (Ex. 11F) | 4.8 | 4.0 | <10 | 395 | 20 | 81 |
| CHO-S | Acid treated | APPC (Ex. 11G) | 4.8 | 12.0 | <10 | 122 | 6.1 | 73 |
| CHO-S | Acid treated | APPC (Ex. 11H) | 4.8 | 12.0 | <10 | 132 | 6.9 | 82 |
| CHO-S | Acid treated | APPC (Ex. 11I) | 4.8 | 12.0 | <10 | 140 | 7.2 | 86 |

Example 13

Depth Filters for the Removal of Aggregated and Small Colloidal Particulates in the Range of 0.1 μm to 200 μm.

The graded depth filter of Example 13 consists of graded non-woven fibers, have a depth of 2 cm, and are capable of filtering an acid flocculated feed stream comprising particles in the range of about 0.1 μm to about 200 μm. The graded depth filter consists of six (6) layers of non-woven fibers from Midwest Filtration Company, Cincinnati, Ohio (2 layers×25 μm, 2 layers×10 μm, 2 layers×5 μm) followed by commercially available cellulose (CE 25)/diatomaceous earth (DE 40), and IM75. The graded depth filter provided herein were assembled in a 23 cm$^2$ integral Mini Cap filtration device (available from Millipore Corporation, Billerica, Mass. USA) and tested for water permeability resulting in a value of 0.25 L/min at 4 psi. Next, acid precipitated unclarified harvest was loaded at 100 L/m$^2$/h until the TMP across any one filter reached 20 psig. Filtration performance was compared against the control graded filter consisting of six (6) layers of non-woven fibers from Midwest Filtration Company, Cincinnati, Ohio (2 layers×25 μm, 2 layers×10 μm, 2 layers×5 μm) followed by a layer of cellulose (CE25), and a layer of diatomaceous earth (DE40). The filter described in this example resulted in a throughput of 11 $V_f/V_m(K=66)$ whereas throughput of control graded depth filter was 12 $V_f/CV_m(K=72)$. However, the graded depth filter described in the example resulted in a turbidity of 1 NTU as compared to 4 NTU for control graded filter. From this comparison, it is evident that Example 13 filter composed of layers as provided herein are capable of removing smaller colloidal particulates in addition to cells and cell debris during clarification which can potentially lead to removal of secondary clarification filters in the process.

Another major benefit for the customer is improved high-solids feedstock clarification economics. As previously noted, in the clarification process applications for many high-solids feedstock, centrifuges and/or tangential flow microfiltration are used as the primary clarification step upstream from the secondary clarification which typically includes a depth filter. By incorporating the depth filter into the primary clarification process in the manner described herein, the preceding (upstream clarification step) and subsequent (downstream clarification step) use of a centrifugation step and/or tangential flow microfiltration step are eliminated. Furthermore, less down time would be anticipated to be spent in cleaning, checking and replacing the centrifuge (s) and/or tangential flow microfiltration membranes.

Example 14

Clarification Depth Filtration Device and System for Purifying a Target Molecule.

FIG. 5 is a schematic representation of an exemplary clarification depth filtration device purification process incorporated into a system for purifying a target molecule, wherein the system includes two or more unit operations connected in fluid communication with each other, in order to perform a process for purifying a target molecule in a continuous or semi-continuous manner. Each unit operation may employ one or more devices to achieve the intended purpose of that unit operation. Accordingly, in some embodiments, the systems described herein, include several devices which are connected to enable the purification process to be run in a continuous or semi-continuous manner.

Without wishing to be bound by theory, it is contemplated that a system can be enclosed in a closed sterile environment, so as to perform the entire purification process in a sterile manner.

In various embodiments, the very first device in such a system is a bioreactor containing the starting material, e.g., culturing cells expressing a protein to be purified. The bioreactor can be any type of bioreactor like a batch or a fed batch bioreactor or a continuous bioreactor like a continuous perfusion fermentation bioreactor. The bioreactor can be made of any suitable material and can be of any size. Typical materials are stainless steel or plastic. In a particular embodiment, the bioreactor is a disposable bioreactor, e.g. in form of a flexible, collapsible bag, designed for single-use.

Clarification may be performed directly in the bioreactor, or alternatively, the bioreactor can simply be used for culturing the cells, and clarification is performed in a different vessel. In yet another embodiment, the cell culture is simply flowed through a clarification depth filtration device as taught herein in order to remove one or more impurities.

Accordingly, in some embodiments, the bioreactor is in fluid communication with a device for performing depth filtration.

The clarification depth filtration device as taught herein is in fluid communication with a device for performing capture using a bind and elute chromatography (e.g., a continuous multi-column chromatography device). In some embodiments, the device for bind and elute chromatography is connected in fluid communication with a unit operation for performing flow-through purification, which may include more than one device/step. In some embodiments, an in-line static mixer or a surge tank is included between the device for bind and elute chromatography and the first device used for flow-through purification.

In some embodiments, the flow-through purification process includes more than one device, e.g., an activated carbon device followed by a AEX chromatography device followed by an in-line static mixer and/or a surge tank for changing pH, followed by a CEX chromatography device followed by a virus filtration device. The devices could generally be in any suitable format, e.g., a column or a cartridge.

The last unit operations in the system may include one or more devices for achieving formulation, which includes diafiltration/concentration and sterile filtration.

Typically, each device includes at least one inlet and at least one outlet, thereby to enable the output from one device to be in fluid communication with the inlet of a consecutive device in the system.

In most processes and systems used in the industry today, each device used in a purification process employs a process equipment unit, also referred to as a "skid," which typically includes the necessary pumps, valves, sensors and device holders. Typically, at least one skid is associated with each device. In some of the embodiments described herein, the number of skids used throughout the purification process is reduced. For example, in some embodiments, only one skid is used to perform the entire flow-through purification process, which may include multiple devices, e.g., activated carbon device, anion exchange chromatography device, cation exchange chromatography device and virus filtration device, along with any equipment needed for solution condition changes. Accordingly, in some embodiments, a single skid may be used for all of the foregoing steps in the flow-through purification process.

In some embodiments, fluid communication between the various devices is continuous; in that the fluid flows directly through all the devices without interruptions. In other embodiments, one or more valves, sensors, detectors, surge tanks and equipment for any in-line solution changes may be included between the various devices, thereby to temporarily interrupt the flow of fluid through the system, if necessary, for example, to replace/remove a particular unit operation.

In some embodiments, one or more surge tanks are included between the various devices. In some embodiments, not more than 3 and not more than 2 surge tanks are present in the entire system.

In some embodiments, a system further includes one or more sensors and/or probes for controlling and/or monitoring one or more process parameters inside the system, for example, temperature, pressure, pH, conductivity, dissolved oxygen (DO), dissolved carbon dioxide ($DCO_2$), mixing rate, flow rate, product parameters. The sensor may also be an optical sensor in some cases.

In some embodiments, process control may be achieved in ways which do not compromise the sterility of the system.

In some embodiments, sensors and/or probes may be connected to a sensor electronics module, the output of which can be sent to a terminal board and/or a relay box. The results of the sensing operations may be input into a computer-implemented control system (e.g., a computer) for calculation and control of various parameters (e.g., temperature and weight/volume measurements, purity) and for display and user interface. Such a control system may also include a combination of electronic, mechanical, and/or pneumatic systems to control process parameters. It should be appreciated that the control system may perform other functions and the invention is not limited to having any particular function or set of functions.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions taught herein.

What is claimed is:

1. A depth filtration device for the primary clarification of a feed containing a target biomolecule of interest and a plurality of cellular debris and/or colloidal particulates without the use of a primary clarification centrifugation step or a primary clarification tangential flow microfiltration step, comprising:
    a graded porous depth filter media, comprising an assembly of individually produced layers, wherein each layer in the graded porous depth filter media is in contact with at least one other layer, selected from the group consisting of:
    (i) from top to bottom, having 2 non-woven fiber layers each having a nominal pore size of 100 μm, followed by 2 non-woven fiber layers each having a nominal pore size of 50 μm followed by 2 non-woven fiber layers each having a nominal pore size of 25 μm, followed by one layer of cellulose and one layer consisting of diatomaceous earth; and
    (ii) from top to bottom, having 2 non-woven fiber layers each having a nominal pore size of 25 μm, followed by 2 non-woven fiber layers each having a nominal pore size of 10 μm, followed by 2 non-woven fiber layers each having a nominal pore size of 5 μm followed by 1 layer of cellulose and 1 layer consisting of diatomaceous earth; and
    (iii) from top to bottom, having 2 non-woven fiber layers each having a nominal pore size of 50 μm, followed by 2 non-woven fiber layers each having a nominal pore size of 25 μm, followed by 2 non-woven fiber layers each having a nominal pore size of 10 μm, followed by 1 layer of cellulose and 1 layer consisting of diatomaceous earth; and
    (iv) from top to bottom, having 2 non-woven fiber layers each having a pore size of 100 μm, followed by 2 non-woven fiber layers each having a pore size of 50 μm, followed by 2 non-woven fiber layers each having a pore size of 25 μm, followed by one layer consisting of diatomaceous earth and one layer comprising cellulose; and
    (v) from top to bottom, having 2 non-woven fiber layers each having a pore size of 35 μm, followed by 2 non-woven fiber layers each having a pore size of 15 μm, followed by 2 non-woven fiber layers each having a pore size of 10 μm, followed by one layer consisting of diatomaceous earth and one layer of cellulose; and
    (vi) from top to bottom, having 2 non-woven fiber layers each having a pore size of 30 μm, followed by 2 non-woven fiber layers each having a pore size of 25 μm, followed by 2 non-woven fiber layers each having a pore size of 20 μm, followed by one layer of cellulose and one layer consisting of diatomaceous earth.

2. The depth filtration device of claim 1 wherein the device has a total thickness of about 0.3 cm to about 3 cm.

3. The depth filtration device of claim 1, wherein the media is anisotropic.

4. The depth filtration device of claim 1, wherein the media comprises a composite of graded layers of non-woven fibers, diatomaceous earth and, optionally, cellulose and the media having an open nominal pore size rating sufficient to filter a chemically flocculated feedstock.

5. The depth filtration device of claim 1, wherein the non-woven fibers are selected from a group consisting of one or more of polypropylene, polyethylene, polyester, or nylon.

6. The depth filtration device of claim 1, wherein the cellular debris and the colloidal particulates have a particle size distribution from about 0.5 μm to about 200 μm, and a mean particle size greater than about 10 μm.

7. The depth filtration device of claim 1, wherein the media provides throughputs greater than 100 L/M2/hr and removes flocculated cellular debris and colloidal particulates having a particle size distribution of about 0.5 μm to about 200 μm from a feedstream by means of filtration.

8. The depth filtration device of claim 7, wherein the feed has greater than 3% solids resulting in a turbidity output less than 20 NTU when a chemical flocculant is added to the feed.

9. The depth filtration device of claim 1, wherein the target biomolecule of interest includes monoclonal antibodies (mAbs), polyclonal antibodies, and biotherapeutics.

10. The depth filtration device of claim 1; and, a bioreactor in fluid communication with said depth filtration device.

* * * * *